United States Patent
Belson et al.

(10) Patent No.: US 9,907,519 B2
(45) Date of Patent: *Mar. 6, 2018

(54) FLUOROSCOPY OPERATOR PROTECTION DEVICE

(71) Applicant: Radiaction Ltd., Tel Aviv (IL)

(72) Inventors: Amir Belson, Los Altos, CA (US); James J. Leary, St. Louis, MO (US)

(73) Assignee: Radiaction Ltd. (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/159,653

(22) Filed: May 19, 2016

(65) Prior Publication Data

US 2016/0262708 A1 Sep. 15, 2016

Related U.S. Application Data

(63) Continuation of application No. 13/874,068, filed on Apr. 30, 2013, now Pat. No. 9,370,331, which is a (Continued)

(51) Int. Cl.
*A61B 6/10* (2006.01)
*A61B 6/00* (2006.01)

(52) U.S. Cl.
CPC .......... *A61B 6/107* (2013.01); *A61B 6/4423* (2013.01); *A61B 6/4441* (2013.01); *A61B 6/487* (2013.01); *A61B 6/589* (2013.01)

(58) Field of Classification Search
CPC ........ A61B 6/107; A61B 6/4423; A61B 6/589
See application file for complete search history.

(56) References Cited

U.S. PATENT DOCUMENTS

| | | | |
|---|---|---|---|
| 2,835,824 A | 5/1958 | Schepker | |
| 3,967,129 A | 6/1976 | Winkler | |
| | (Continued) | | |

FOREIGN PATENT DOCUMENTS

| | | |
|---|---|---|
| FR | 2736256 | 1/1997 |
| JP | 07-39805 | 7/1995 |
| | (Continued) | |

OTHER PUBLICATIONS

European search report and search opinion dated Feb. 19, 2013 for EP Application No. 07874128.7.
(Continued)

*Primary Examiner* — Glen Kao
(74) *Attorney, Agent, or Firm* — Wilson Sonsini Goodrich & Rosati

(57) ABSTRACT

A radiation protection device attaches to the C-arm of a fluoroscope and shields and collimates the X-ray beam between the X-ray source and the patient and between the patient and the image intensifier. One embodiment has a radiation shield of X-ray opaque material that surrounds the C-arm of the fluoroscopy system, the X-ray source and the image intensifier. A padded slot fits around the patient's body. Another embodiment has conical or cylindrical radiation shields that extend between the X-ray source and the patient and between the patient and the image intensifier. The radiation shields have length adjustments and padded ends to fit the device to the patient. The radiation protection device may be motorized to advance and withdraw the radiation shields. A blanket-like radiation shield covers the patient in the area surrounding where the X-ray beam enters the body.

8 Claims, 24 Drawing Sheets

Related U.S. Application Data continuation of application No. 13/344,426, filed on Jan. 5, 2012, now Pat. No. 8,439,564, which is a continuation of application No. 12/313,782, filed on Nov. 21, 2008, now Pat. No. 8,113,713, which is a continuation-in-part of application No. PCT/US2007/023892, filed on Nov. 7, 2007.

(60) Provisional application No. 60/858,058, filed on Nov. 11, 2006, provisional application No. 60/923,481, filed on Apr. 13, 2007.

(56) References Cited

U.S. PATENT DOCUMENTS

| | | | |
|---|---|---|---|
| 3,984,695 | A | 10/1976 | Collica et al. |
| 3,984,696 | A | 10/1976 | Collica et al. |
| 4,062,518 | A | 12/1977 | Stivender et al. |
| 4,122,350 | A | 10/1978 | Lipthay et al. |
| 4,140,129 | A | 2/1979 | Heinz et al. |
| 4,210,811 | A | 7/1980 | Dennhoven et al. |
| 4,581,538 | A | 4/1986 | Lenhart |
| 4,795,654 | A | 1/1989 | Teleki |
| 4,938,233 | A | 7/1990 | Orrison, Jr. |
| 4,969,170 | A | 11/1990 | Kikuchi et al. |
| 4,977,585 | A | 12/1990 | Boyd |
| 5,006,718 | A | 4/1991 | Lenhart |
| 5,299,243 | A | 3/1994 | Picco |
| 5,335,366 | A | 8/1994 | Daniels |
| 5,417,225 | A | 5/1995 | Rubenstein et al. |
| 5,651,044 | A | 7/1997 | Klotz, Jr. et al. |
| 5,900,638 | A | 5/1999 | Jaeger et al. |
| 5,981,964 | A | 11/1999 | Mcauley et al. |
| 6,325,538 | B1 | 12/2001 | Heesch |
| 6,352,363 | B1 | 3/2002 | Munger et al. |
| 6,448,571 | B1 | 9/2002 | Goldstein |
| 6,456,684 | B1 | 9/2002 | Mun et al. |
| 6,481,888 | B1 | 11/2002 | Morgan |
| 6,636,757 | B1 | 10/2003 | Jascob et al. |
| 6,653,648 | B2 | 11/2003 | Goldstein |
| 6,674,087 | B2 | 1/2004 | Cadwalader et al. |
| 6,703,632 | B1 | 3/2004 | Macklis et al. |
| 7,057,194 | B2 | 6/2006 | Goldstein |
| 7,091,508 | B2 | 8/2006 | Goldstein |
| 7,108,422 | B2 | 9/2006 | Borom |
| 7,331,712 | B2 | 2/2008 | Fischer et al. |
| 7,391,042 | B2 | 6/2008 | Goldstein |
| 7,420,193 | B2 | 9/2008 | Treuth |
| 7,440,539 | B2 | 10/2008 | Danielsson et al. |
| 7,648,273 | B2 | 1/2010 | Manzke et al. |
| 7,829,873 | B2 | 11/2010 | Fox et al. |
| 8,113,713 | B2 | 2/2012 | Belson et al. |
| 8,439,564 | B2 | 5/2013 | Belson et al. |
| 9,370,331 | B2 | 6/2016 | Belson et al. |
| 2002/0003854 | A1 | 1/2002 | Ivan et al. |
| 2002/0015471 | A1 | 2/2002 | Yagi |
| 2002/0193686 | A1 | 12/2002 | Gilboa |
| 2005/0070779 | A1 | 3/2005 | Singh et al. |
| 2005/0213713 | A1 | 9/2005 | Cadwalader et al. |
| 2005/0236588 | A1 | 10/2005 | Ein-Gal |
| 2006/0076522 | A1 | 4/2006 | Goldstein |
| 2006/0251219 | A1 | 11/2006 | Cadwalader et al. |
| 2006/0262898 | A1 | 11/2006 | Partain et al. |
| 2006/0284123 | A1 | 12/2006 | Goldstein |
| 2007/0029513 | A1 | 2/2007 | Treuth |
| 2007/0086570 | A1 | 4/2007 | Spahn |
| 2007/0189442 | A1 | 8/2007 | Sukovic et al. |
| 2008/0093568 | A1 | 4/2008 | Fox et al. |
| 2009/0010389 | A1 | 1/2009 | Ma et al. |
| 2009/0232282 | A1 | 9/2009 | Belson et al. |
| 2010/0133450 | A1 | 6/2010 | Belson et al. |
| 2012/0106715 | A1 | 5/2012 | Belson et al. |
| 2014/0153700 | A1 | 6/2014 | Belson et al. |

FOREIGN PATENT DOCUMENTS

| | | |
|---|---|---|
| JP | 2004-506911 | 3/2004 |
| JP | 2004-264207 | 9/2004 |
| JP | 2005-177047 | 7/2005 |
| WO | WO 03/073939 A1 | 9/2003 |
| WO | WO 2005/102174 A1 | 11/2005 |
| WO | WO 2006/026646 A1 | 3/2006 |
| WO | WO 2006/092078 AI | 9/2006 |
| WO | WO 2007/060561 A2 | 5/2007 |
| WO | WO 2007/060561 A3 | 10/2007 |

OTHER PUBLICATIONS

International search report and written opinion dated Oct. 9, 2008 for PCT/US2007/023892.
Notice of allowance dated Jan. 17, 2013 for U.S. Appl. No. 13/344,426.
Notice of allowance dated Mar. 2, 2016 for U.S. Appl. No. 13/874,068.
Notice of allowance dated Nov. 21, 2011 for U.S. Appl. No. 12/313,782.
Office action dated Mar. 20, 2014 for U.S. Appl. No. 13/874,068.
Office action dated May 19, 2014 for U.S. Appl. No. 13/874,068.
Office action dated Aug. 2, 2012 for U.S. Appl. No. 13/344,426.
Office action dated Sep. 2, 2011 for U.S. Appl. No. 12/313,782.
Office action dated Oct. 7, 2011 for U.S. Appl. No. 12/447,833.

FLUOROSCOPY OPERATOR PROTECTION DEVICE

CROSS REFERENCE TO RELATED APPLICATIONS

This application is a continuation of U.S. patent application Ser. No. 13/874,068, filed Apr. 30, 2013, now U.S. Pat. No. 9,370,331, which is a continuation of U.S. patent application Ser. No. 13/344,426, filed Jan. 5, 2012, now U.S. Pat. No. 8,439,564, which is a continuation of U.S. patent application Ser. No. 12/313,782, filed Nov. 21, 2008, now U.S. Pat. No. 8,113,713, which is a continuation-in-part of PCT/US2007/023892, filed Nov. 7, 2007, which claims the benefit of Provisional Application No. 60/858,058, filed on Nov. 11, 2006, and Provisional Application No. 60/923,481, filed on Apr. 13, 2007, the full disclosures of which are incorporated herein by reference.

BACKGROUND OF THE INVENTION

Field of the Invention

The present invention relates to radiation protection devices to protect fluoroscopy operators and other medical personnel from radiation exposure during fluoroscopic imaging procedures.

Fluoroscopy, a real-time X-ray imaging technique, has long been important as a medical diagnostic tool, particularly in disciplines where still X-rays do not provide sufficient diagnostic information of the movement and function of living, moving organs. Fluoroscopy is widely used in cardiology, electrophysiology, gastroenterology and orthopedics. With the recent growth in catheter-based interventional cardiology and radiology procedures, there has been a tremendous increase in the use of fluoroscopy. Many life saving interventional procedures would not be possible without the use of fluoroscopy. However, fluoroscopic imaging exposes the patient and attendant medical personnel to potentially harmful X-ray radiation. For the patient, some exposure to X-rays is necessary to produce the fluoroscopic images and the exposure is usually brief and infrequent. The benefit to the patient is sufficient to outweigh the potentially harmful effects of the X-ray radiation. However, medical personnel involved in fluoroscopic imaging are exposed to significant doses of X-ray radiation on a daily basis. This is particularly true for interventional cardiologists and radiologists who must work in close proximity to the patient who is undergoing fluoroscopic imaging and for orthopedists manipulating a joint while observing it under fluoroscopy.

X-ray exposure to medical personnel comes from two sources, direct exposure to the X-ray beam and scattered X-rays. Direct exposure occurs when the operator's hands or other body parts are placed in the X-ray beam while the fluoroscope is operating. X-ray scattering occurs when X-rays strike electrons in the patient's tissue and are deflected back and to the sides at angles that are not parallel to the incident beam. While scattered X-rays are much lower intensity than the direct X-ray beam, it is much more likely for the operator to be exposed to scattered X-rays and the damaging effects are cumulative from months and years of exposure.

Most states require that all medical personnel who work in the room during fluoroscopy wear protective equipment, typically a radiation resistant apron or the like providing protection equivalent to 0.25-0.5 mm of lead, depending on state regulations and the intensity of the X-ray source utilized. Depending on the thickness used, lead aprons absorb 90-99 percent of X-ray radiation striking the apron. However, they only protect the areas of the body that are covered and it is recommended that personnel who work frequently and in close proximity to the fluoroscope also wear additional protection, such as thyroid protectors, lead filled glasses and face shields. Exposed areas of the body are still susceptible to X-ray exposure.

Though necessary for radiation protection, the lead aprons are heavy and uncomfortable, resulting in fatigue and injuries. Back, knee and ankle injuries are common among personnel who frequently work in the fluoroscopy laboratory with a lead apron on. X-ray exposure, fatigue and injuries would all be expected to increase for operators involved in long, complex interventional procedures requiring fluoroscopic imaging.

Due to the incomplete radiation protection provided by lead aprons and leaded glasses and the increased likelihood of fatigue and injuries, it would be desirable to provide a radiation protection device that provides more complete protection and that reduces or eliminates the necessity for using heavy radiation protection garments. Such a device would ideally protect the fluoroscope operator and all nearby personnel from direct exposure to the X-ray beam and from scattered X-rays. The device should not interfere with the performance of the fluoroscopy or any diagnostic or therapeutic procedures performed during fluoroscopy. Preferably, the device would be free of other inconveniences to the operator or the patient. A truly effective radiation protection device could reduce the overall cost of radiation protection by eliminating the need for lead aprons and other protective gear and could even simplify the construction of the fluoroscopy suite in the hospital by decreasing the amount of radiation shielding necessary.

BRIEF SUMMARY OF THE INVENTION

In keeping with the foregoing discussion, the present invention provides a radiation protection device with one or more radiation shields that attach to the C-arm of the fluoroscopy system and shields and collimates the X-ray beam between the X-ray source and the patient and between the patient and the image intensifier. This will protect the operator from inadvertently being exposed to the direct X-ray beam and will eliminate a significant percentage of the scattered X-rays. To eliminate the remainder of the scattered X-rays that emanate from the patient, the radiation protection device may also include a blanket-like radiation shield that covers the patient in the area surrounding where the X-ray beam enters the body. Optionally, the blanket-like radiation shield may be connected to the radiation shield(s) on the C-arm.

In one embodiment, the radiation protection device has a radiation shield of X-ray opaque material that surrounds the C-arm of the fluoroscopy system, the X-ray source and the image intensifier. A slot or opening is provided to fit the radiation shield around the patient's body. A soft, flexible material surrounds the opening to comfortably fit the radiation shield to the contours of the patient's body and to accommodate some motion of the C-arm relative to the patient.

In another embodiment, the radiation protection device has a first conical or cylindrical radiation shield that extends from the X-ray source to the patient or to the procedure table and a second conical or cylindrical radiation shield that extends from the patient to the image intensifier. The first radiation shield and the second radiation shield have length or height adjustments to fit the device to the patient and to accommodate motion of the C-arm relative to the patient. A soft, flexible material surrounds the openings of the first radiation shield and the second radiation shield to comfortably fit them to the contours of the patient's body. Optionally, the radiation protection device has electric motors or the like for withdrawing and advancing the first radiation shield and the second radiation shield from contact with the patient so that the C-arm can be freely moved and repositioned relative to the patient. Optionally, the second radiation shield may have one or more hand ports to allow the operator to work on the area of the patient under the second radiation shield without withdrawing it from contact with the patient. Each embodiment of the radiation protection device may also include a blanket-like radiation shield that covers the patient in the area surrounding where the X-ray beam enters the body.

DETAILED DESCRIPTION OF THE INVENTION

Figure 1:
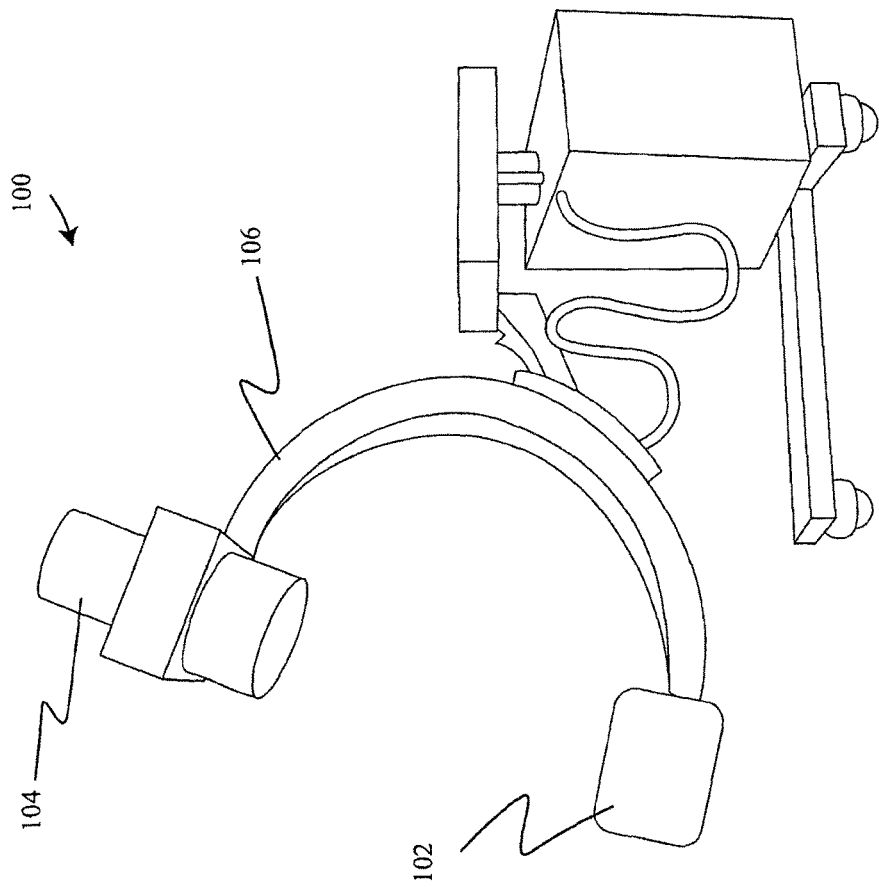
FIG. 1 illustrates a prior art C-arm fluoroscopy system.
Figure 1:
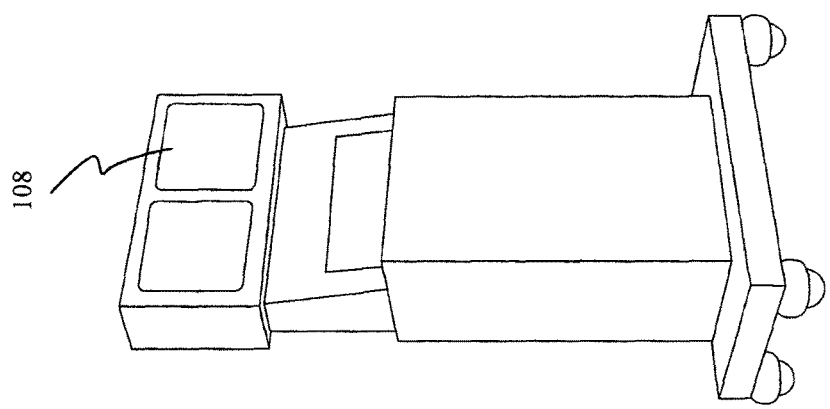

FIG. 1 illustrates a prior art C-arm fluoroscopy system 100. The fluoroscope 100 includes an X-ray source 102 and an image intensifier 104 mounted on opposite ends of a C-arm 106. The C-arm 106 may be mounted on a mobile base with wheels, as shown, or it may be mounted via a support arm to the floor or the ceiling of the fluoroscopy suite. In use, the X-ray source 102 and the image intensifier 104 are placed on opposite sides of the portion of the patient's body to be imaged. The X-ray source 102 directs an X-ray beam through the patient's body toward the image intensifier 104, which captures the X-ray image and displays it on a monitor 108 in real time. Often, the X-ray source 102 is positioned below the patient and the image intensifier 104 is positioned above as shown, however for some applications these positions may be reversed or the C-arm 106 may be positioned horizontally or at an oblique angle. The system may also include electronic memory for storing and replaying fluoro images and a cine camera for capturing fluoro images on film. For catheterization laboratory use, the C-arm 106 will be mounted beside or at the head end of a procedure table. The C-arm 106 can be moved and rotated to position the X-ray source 102 and the image intensifier 104 for the best images of the target anatomy. Often, the X-ray source 102 is positioned below the patient and the image intensifier 104 is positioned above as shown, however for some applications these positions may be reversed or the C-arm 106 may be positioned horizontally or at an oblique angle.

Figure 2:
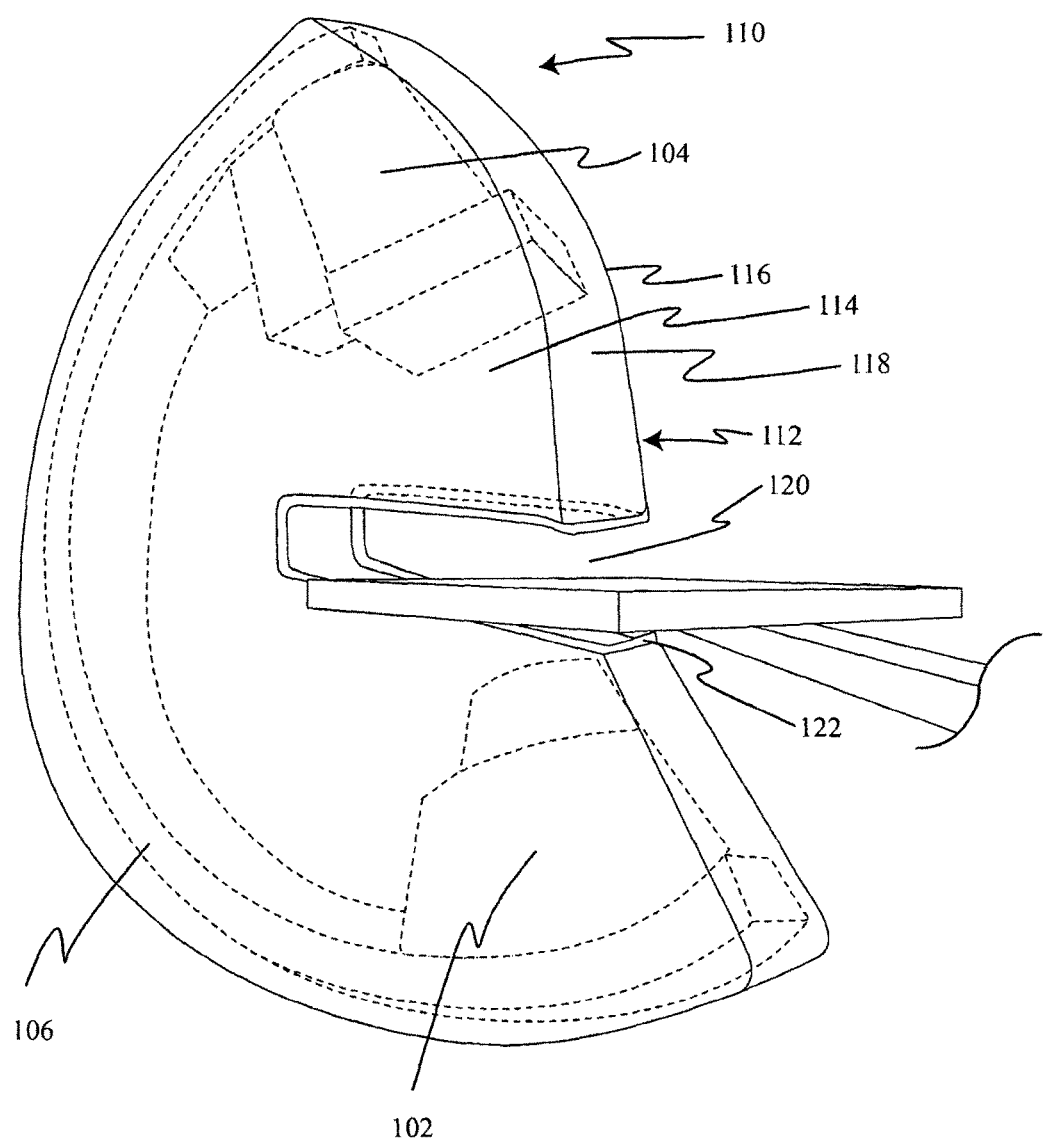
FIG. 2 illustrates one embodiment of the radiation protection device mounted on the C-arm of the fluoroscopy system.

FIG. 2 illustrates one embodiment of the radiation protection device 110 mounted on the C-arm 106 of the fluoroscopy system 100. The radiation protection device 110 includes a radiation shield 112 of X-ray opaque material that surrounds the C-arm 106 of the fluoroscopy system 100, the X-ray source 102 and the image intensifier 104. The radiation shield 112 has a first approximately planar side wall 114 and a second approximately planar side wall 116 joined together by a peripheral wall 118. A slot or opening 120 through the first and second side walls 114, 116 and the peripheral wall 118 is provided to fit the radiation shield 112 around the patient's body and, optionally, the procedure table, as appropriate for the intended use. The back side of the peripheral wall 118 will have an opening or extended slot 126 for the support arm 128 that holds the C-arm 106. A pad 122 of soft, flexible material surrounds the opening 120 to comfortably fit the radiation shield to the contours of the patient's body and to accommodate some motion of the C-arm 106 relative to the patient. Optionally, the opening 120 can be covered with a material that is transparent to X-rays. The pad 122 around the opening 120 may be an inflatable or foam-filled rim of lead-filled rubber or other soft, conformable structure. The radiation protection device 110 may be joined directly to the C-arm 106 with fasteners and/or adhesives or it may be an independent structure that can be placed on and removed from the C-arm 106, for example with zippers, magnets, snaps, straps, hook-and-loop fasteners, etc.

The radiation shield(s) in this and other embodiments may be made with lead shielding, a composite material or other X-ray opaque material. Preferably, the radiation shielding material will provide protection equivalent to 0.5 mm of lead or greater so that additional radiation protection will not be needed. For example, U.S. Pat. No. 4,795,654 describes a composite X-ray opaque material with a triple layer structure. The first layer can be built from uranium, lead and gold among others. The second layer may be made of tin, and indium among others and the third layer made of zinc, copper, nickel and chromium among others. Alternatively, a polymer shielding material filled with X-ray opaque materials may have weight, manufacturing and structural advantages over a metallic shielding material. Optionally, the shielding material may be flexible, such as lead filled rubber or plastic, and it may be optically transparent, such as lead filled glass or a transparent X-ray opaque plastic. For example, flexible and rigid polymeric X-ray opaque materials sold under the tradename DEMRON are available from Radiation Shielding Technologies, Coral Gables, Fla. and described in U.S. Pat. Nos. 6,841,791, 6,828,578, 6,459,091, 6,281,515 and 7,196,023.

Figure 3:
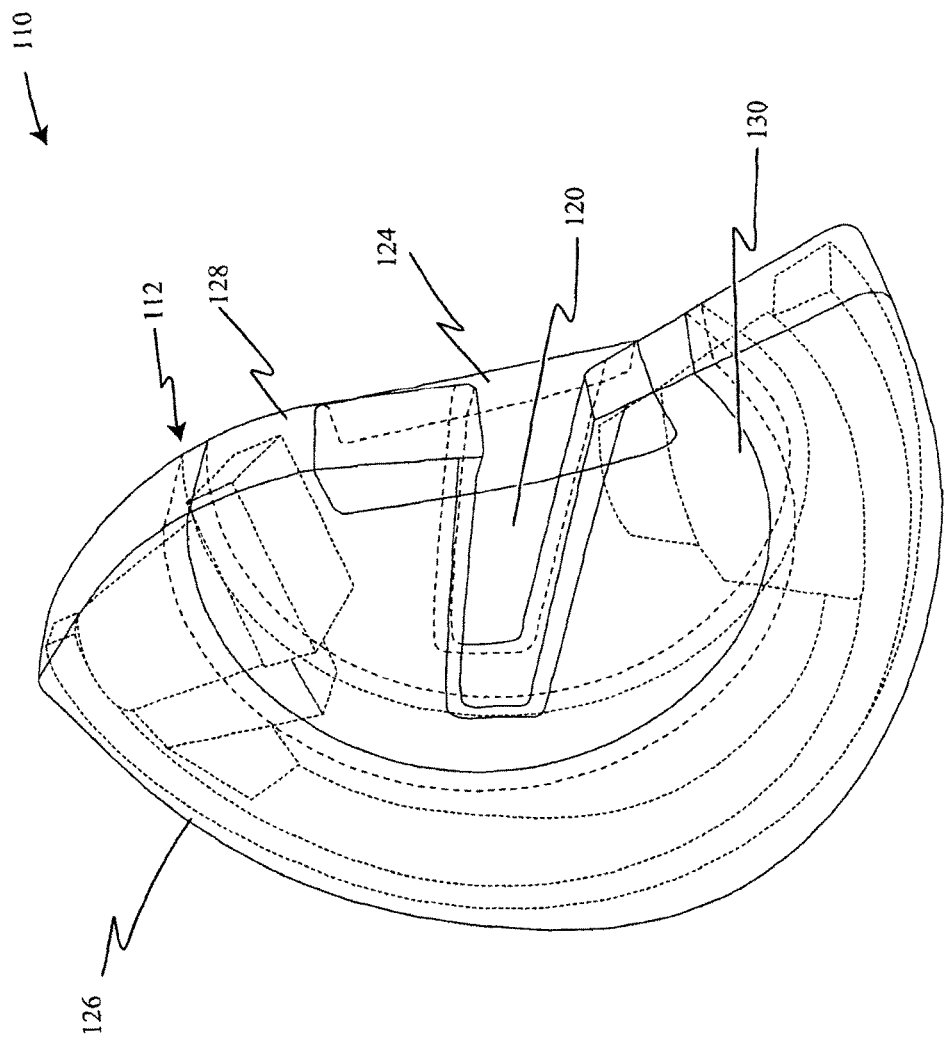
FIG. 3 illustrates a variation of the radiation protection device of FIG. 2.

FIG. 3 illustrates a variation of the radiation protection device 110 of FIG. 2 in which the radiation shield 112 has a C-arm attached portion 126 and a patient-stationary portion 128. An overlapping, sliding joint 130 between the C-arm attached portion 126 and the patient-stationary portion 128 allows a greater range of motion of the C-arm 106 relative to the patient. Optionally, a flap 124 of X-ray opaque material, preferably a flexible material, may be provided to cover a portion of the opening 120 after it has been passed around a body part. The flap 124 may be removably attached, for example using magnets, snaps or hook-and-loop fasteners.

In an alternate embodiment of the radiation protection device 110 of FIG. 2, the radiation shield 112 may be independently supported, so that it is held stationary relative to the patient, allowing the C-arm 106 to move independently within the radiation shield 112.

Figure 4:
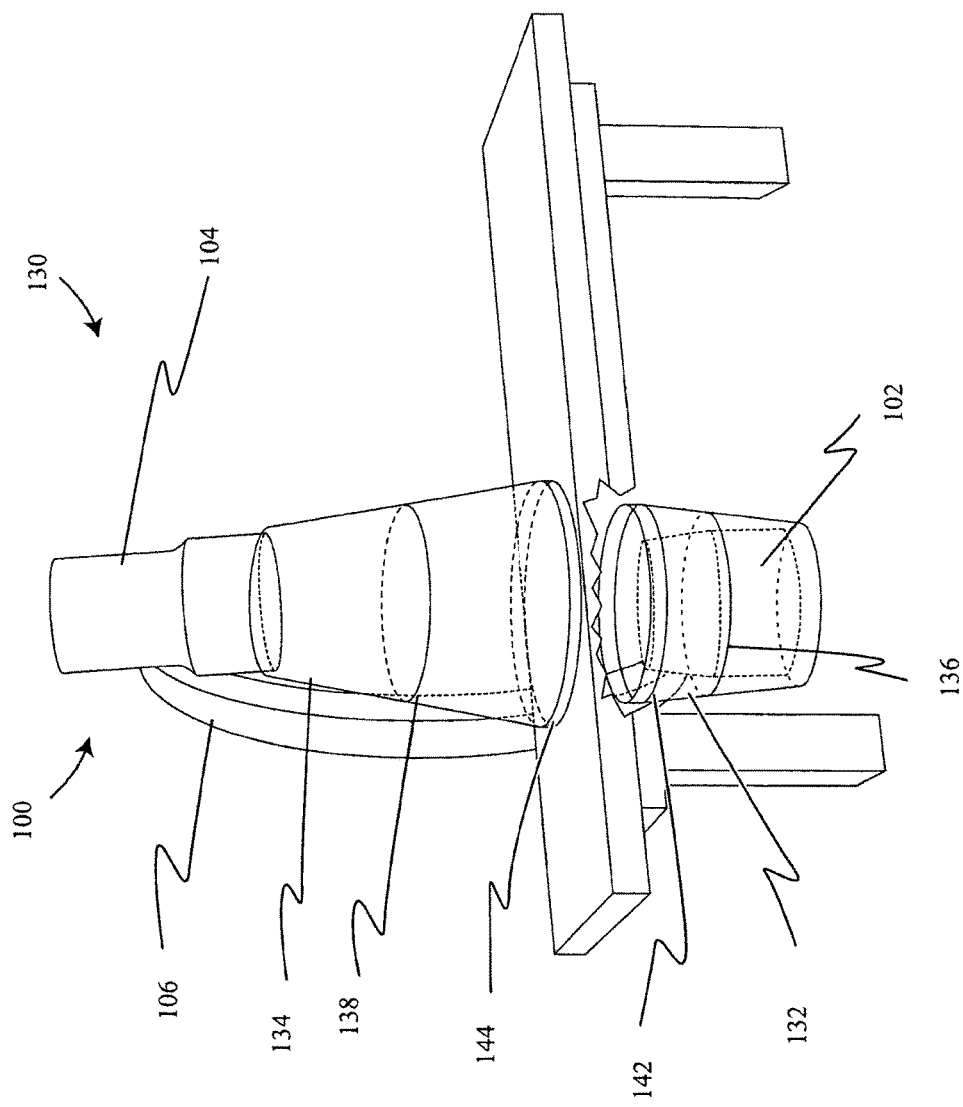
FIG. 4 illustrates an embodiment of the radiation protection device with a first radiation shield and a second radiation shield mounted on the C-arm of the fluoroscopy system.

FIG. 4 illustrates an embodiment of the radiation protection device 130 with a first radiation shield 132 and a second radiation shield 134 mounted on the C-arm 106 of the fluoroscopy system 100. The first radiation shield 132 is approximately conical or cylindrical in shape and extends from the X-ray source 102 to the patient, or to the procedure table 140 as appropriate for the body part being imaged. The second radiation shield 134 is also approximately conical or cylindrical in shape and extends from the image intensifier 104 to the patient. The radiation shields 132, 134 are typically open on the ends closest to the patient, but, optionally, the openings can be covered with a material that is transparent to X-rays.

The first radiation shield 132 and the second radiation shield 134 have length or height adjustments 136, 138 to fit the device to the patient and to accommodate motion of the C-arm 106 relative to the patient. The length or height adjustments 136, 138 may be configured as overlapping telescopic joints, expandable bellows joints or the like. A pad 142, 144 of soft, flexible material surrounds the openings of the first radiation shield 132 and the second radiation shield 134 to comfortably fit them to the contours of the patient's body. The pads 142, 144 around the openings may be an inflatable or foam-filled rim of lead-filled rubber or other soft, conformable structure. The conformable pads 142, 144 may be shaped as bellows of flexible X-ray opaque material. Alternatively or in addition, the conformable pads 142, 144 may be configured as inflatable tubes or bellows filled with an X-ray opaque liquid. The length or height adjustments 136, 138 and the conformable pads 142, 144 allow for a significant degree of repositioning of the C-arm 106 relative to the patient without having to readjust the radiation shields 132, 134. Optionally, the length or height adjustments 136, 138 may be spring loaded with a light spring force to keep the radiation shields 132, 134 in contact with the patient when the C-arm 106 is adjusted without causing discomfort to the patient. For major repositioning of the C-arm 106, the radiation shields 132, 134 will preferably be withdrawn from contacting the patient in order to allow free motion of the C-arm 106.

Figure 5:
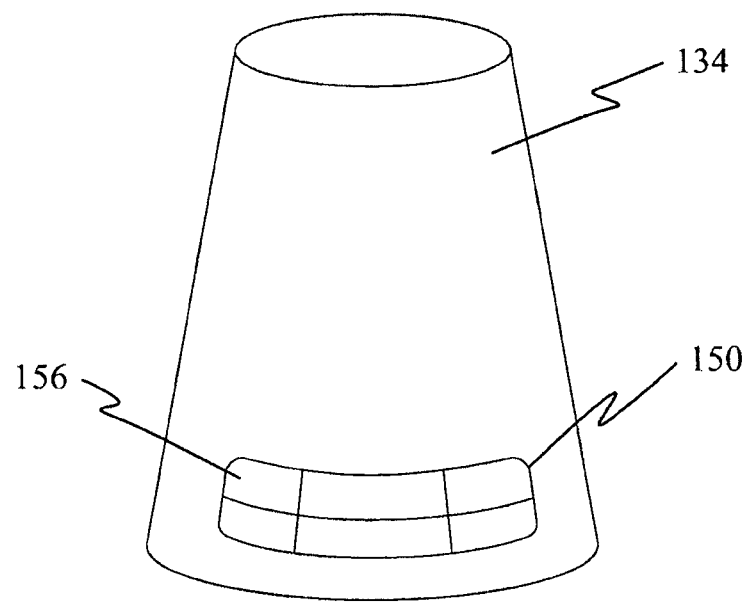
FIG. 5 illustrates a radiation shield with a hand port.

Optionally, the second radiation shield 134 may have one or more hand ports to allow the operator to work on the area of the patient under the second radiation shield 134 without withdrawing it from contact with the patient. FIG. 5 illustrates a radiation shield 134 with a single hand port 150 large enough for both of the operator's hands and/or one or more instruments to fit through. The hand port 150 is preferably fitted with a closure 156 of radiation shielding material to prevent X-rays from escaping through the hand port 150. In one preferred embodiment, the closure comprises a plurality of overlapping flaps of flexible radiation shielding material that will allow a hand or instrument to pass through and will seal around the hand or instrument.

Figure 6:
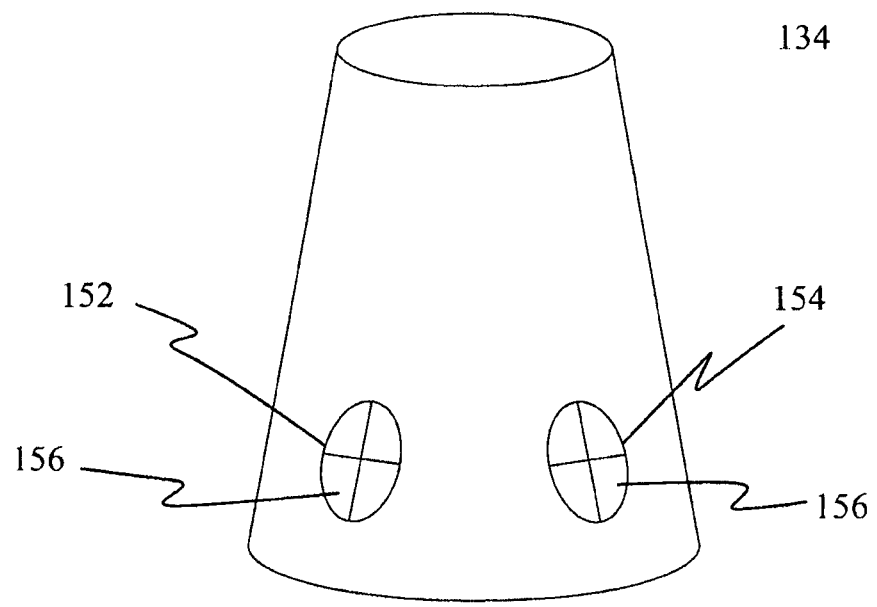
FIG. 6 illustrates a radiation shield with two hand ports.

FIG. 6 illustrates a radiation shield with two hand ports 152, 154. Each of the hand ports 152, 154 is preferably fitted with a closure 156 of radiation shielding material to prevent X-rays from escaping through the hand ports 152, 154.

Preferably, when a hand port is included in the radiation protection device 130, at least a portion of the radiation shield 134 will be made of transparent radiation shielding material so that the operator can see the area under the radiation shield 134. If the operator needs to have the hands inside of the radiation shield 134 while the fluoroscope 100 is operating, it is highly recommended that radiation shielding gloves be worn. In an alternate embodiment, a pair of radiation shielding gloves could be incorporated into the hand ports 152, 154.

Figure 7:
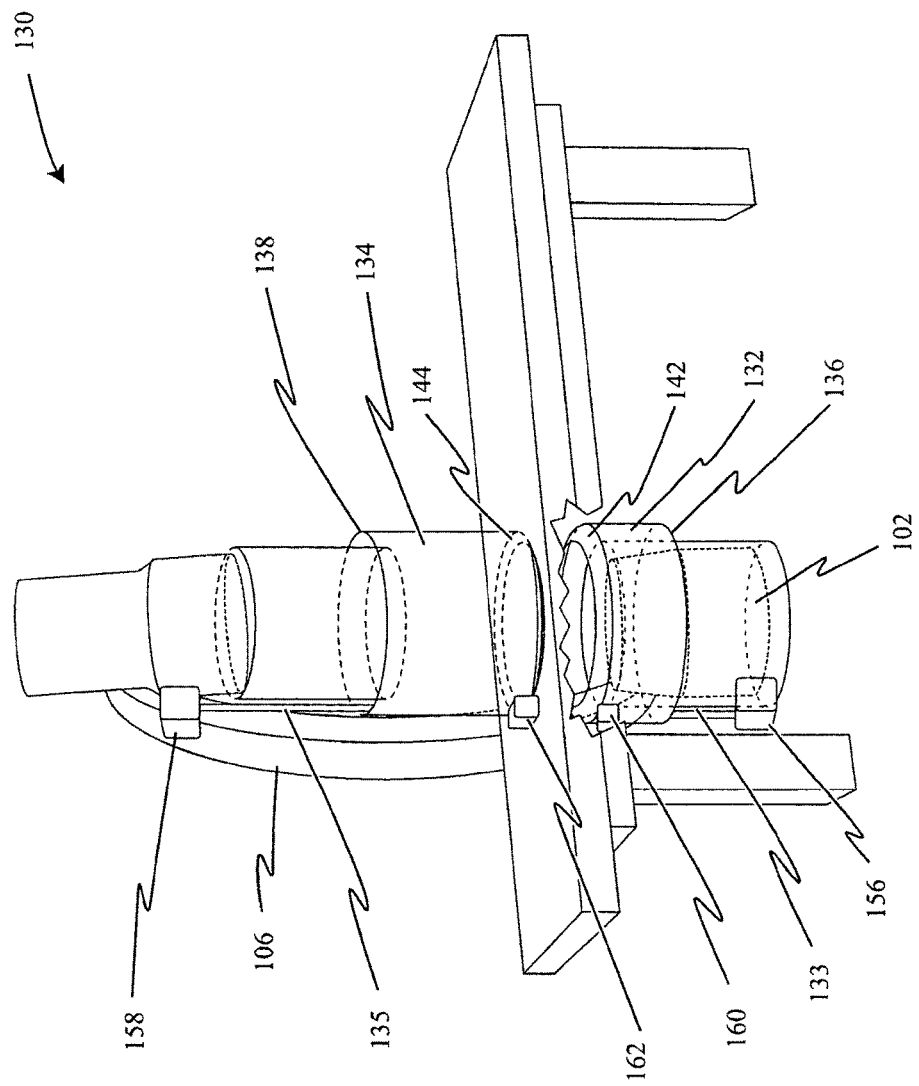
FIG. 7 illustrates an embodiment of the radiation protection device with motors for extending and retracting the first radiation shield and the second radiation shield.

Optionally, the radiation protection device 130 may be motorized for extending and retracting the first radiation shield 132 and the second radiation shield 134 from contact with the patient so that the C-arm can be freely moved and repositioned relative to the patient. FIG. 7 illustrates an embodiment of the radiation protection device 130 with motors 156, 158 for extending and retracting the first radiation shield 132 and the second radiation shield 134. The motors 156, 158 may be electric motors with a rack and pinion mechanism, a scissors mechanism, or other mechanism 133, 135 for translating the rotary motion of the motor into linear motion of the radiation shields 132, 134. Optionally, the operating mechanism may be spring loaded with a light spring force to keep the radiation shields 132, 134 in contact with the patient when the C-arm 106 is adjusted without causing discomfort to the patient. For major repositioning of the C-arm 106, the radiation shields 132, 134 will preferably be withdrawn from contacting the patient in order to allow free motion of the C-arm 106. Alternatively, pneumatic or hydraulic actuators may be used in place of the electric motors.

Preferably, the radiation protection device 130 will also include sensors 160, 162, such as proximity sensors, optical sensors, contact sensors, etc., that will stop the telescopic extension of the radiation shields 132, 134 when they are in the right contact with the patient. One option would be to have the conforming pads 142, 144 around the openings of the radiation shields 132, 134 mechanized to operate in a coordinated sequence with the extension and retraction of the radiation shields 132, 134. In one example, the conforming pads 142, 144 could be inflatable. The radiation shields 132, 134 would extend telescopically with the pads 142, 144 deflated until the sensors 160, 162 detect close proximity or initial contact with the patient's body, then the radiation shields 132, 134 would stop extending and the pads 142, 144 would inflate to close any gap left between the radiation shields 132, 134 and the patient.

Alternately or in addition, force sensors connected with the motors 156, 158 could be used to sense when the radiation shields 132, 134 are in contact with the patient.

An interlock switch could be included to prevent the fluoroscope 100 from operating unless the sensors 160, 162 confirm that the radiation shields 132, 134 are in contact with the patient's body. In addition, one or more X-ray detectors could be positioned on or near the radiation protection device 130 outside of the radiation shields 132, 134 to detect X-ray leakage and connected to an interlock switch that shuts down the X-ray source if stray X-ray radiation is detected.

Each embodiment of the radiation protection device may also include a blanket-like radiation shield that covers the patient in the area surrounding where the X-ray beam enters the body. Optionally, the blanket-like radiation shield may be connected to the radiation shield(s) on the C-arm.

Figure 8:
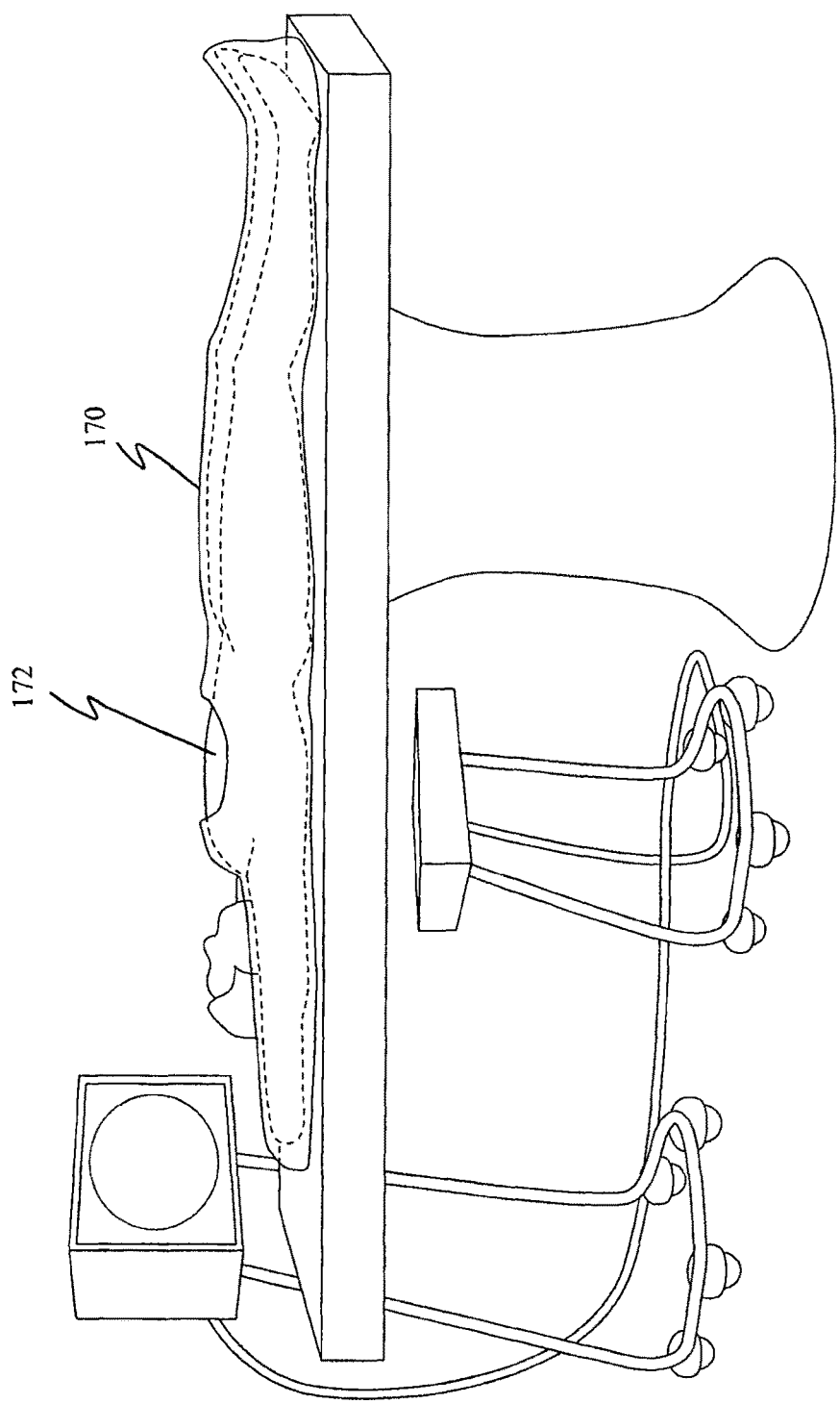
FIG. 8 illustrates a blanket-like radiation shield that covers the patient except the area that is being imaged.

FIG. 8 illustrates a blanket-like radiation shield 170 that covers the patient except the area that is being imaged. The blanket-like radiation shield 170 is preferably made of a flexible X-ray opaque material that covers most of the patient, except a fenestrated area 172 over the portion of the patient that is to be imaged. For catheter procedures, a second fenestration may be positioned over the vascular access site, for example the femoral or brachial artery or the jugular vein. Preferably, the radiation shielding material will provide protection equivalent to 0.5 mm of lead or greater. Because scattered X-rays are only partially attenuated in the body, this level of protection will preferably extend at least to areas of the body within a meter of where the X-ray beam enters the patient's body. Optionally, the blanket-like radiation shield 170 may have a removable cover for patient comfort and for ease in sanitizing the patient-contact portions of the device. The removable cover may be washable and reusable or it may be a single-use sterile disposable cover.

Figure 9:
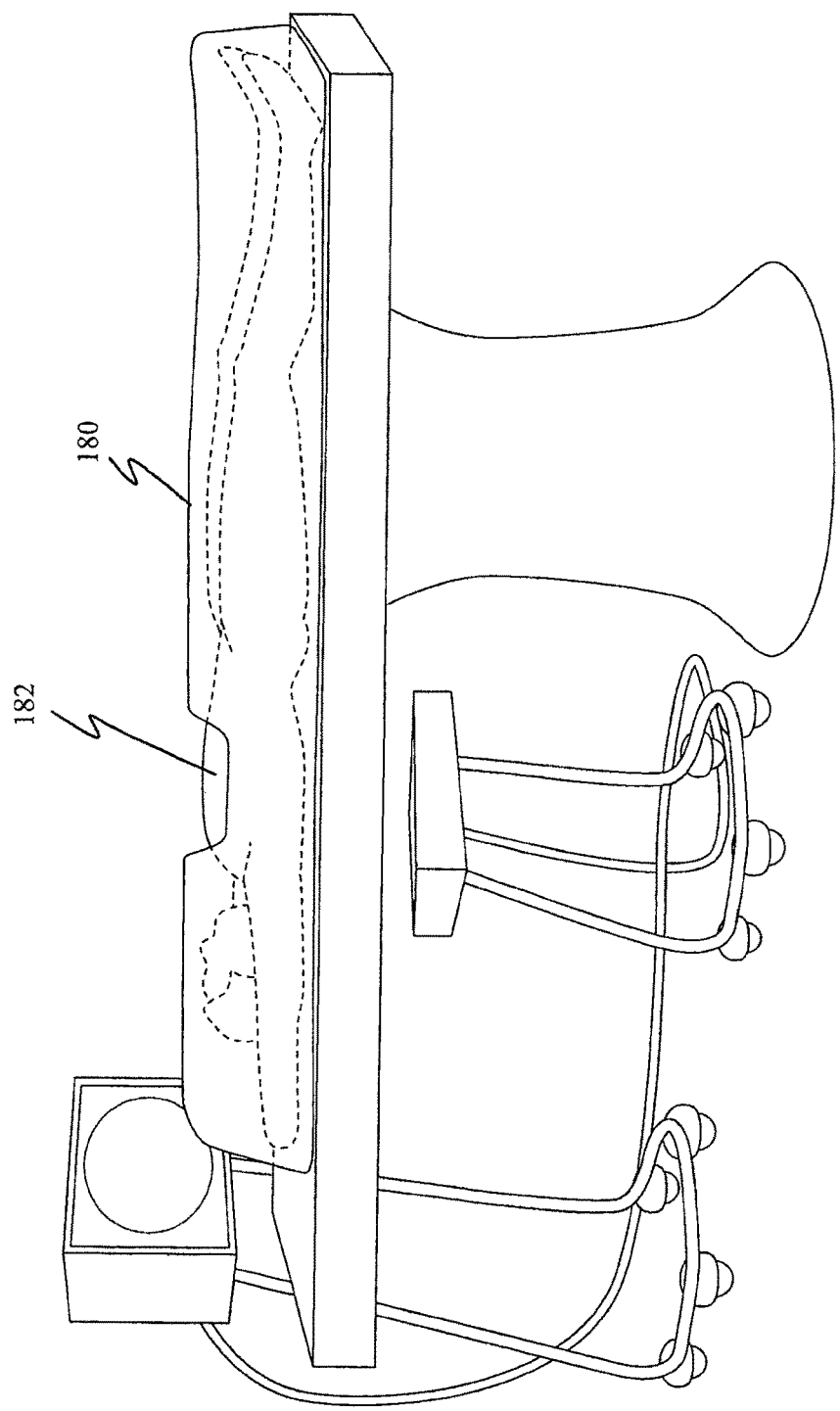
FIG. 9 illustrates a radiation shield elevated slightly above and surrounding the patient.

FIG. 9 illustrates a radiation shield 180 elevated slightly above and surrounding the patient, except a fenestrated area 182 over the portion of the patient that is to be imaged. If a rigid radiation shielding material is used, the radiation shield 180 may be self-supporting. Otherwise, a flexible radiation shielding material may be supported on a frame over the patient.

In addition, another radiation shield may extend under the patient, with another fenestration under the portion of the patient to be imaged. Optionally, this radiation shield may be an extension of the blanket-like radiation shield 170, 180 that is over the patient. Alternatively, the procedure table may be made partially of radiation shielding material with an X-ray transparent portion beneath the portion of the patient to be imaged, however this option potential limits the usability of the procedure table for different types of procedures. Optionally, the blanket-like radiation shield 170, 180 may fasten to one or both of the radiation shields of the radiation protection device.

Figure 10:
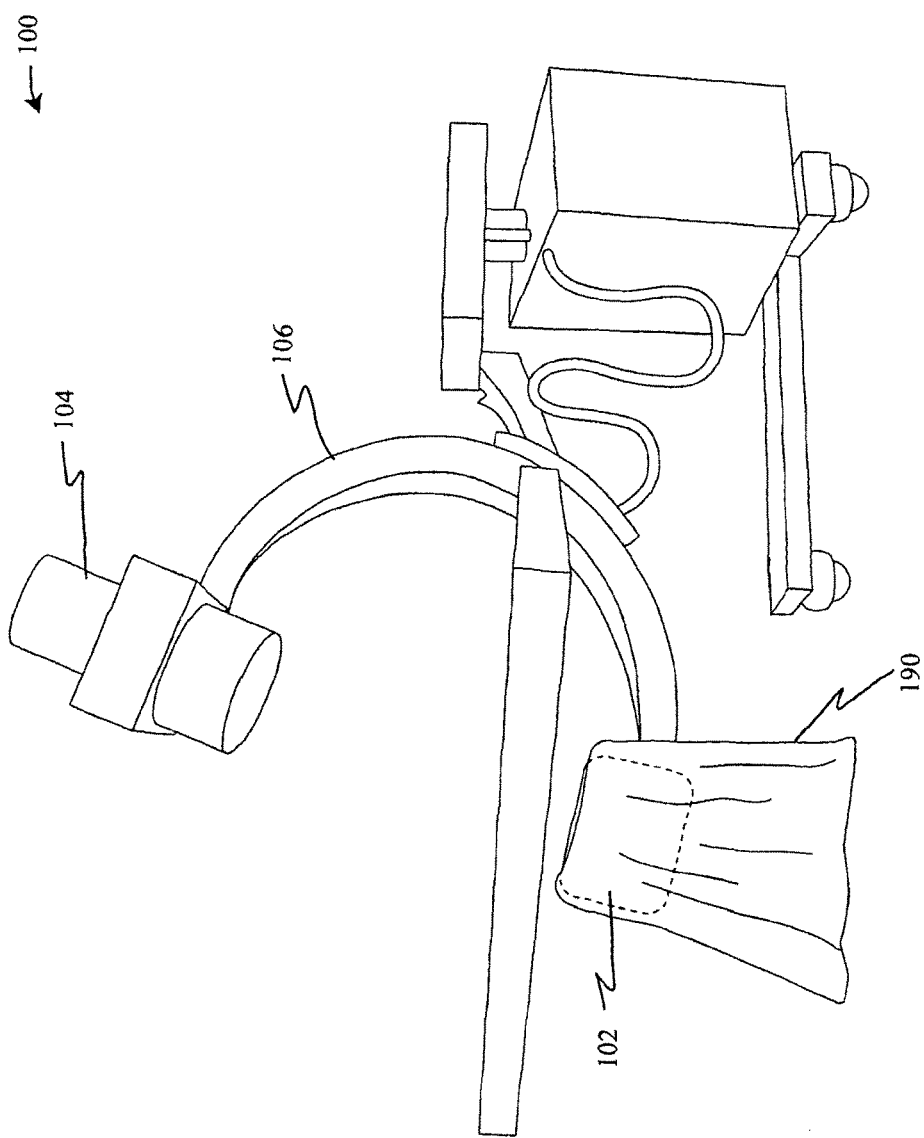
FIG. 10 illustrates a radiation shield suspended from the X-ray source of the fluoroscopy system.

FIG. 10 illustrates a radiation shield 190 suspended from the X-ray source 102 of the fluoroscopy system 100. This is a curtain-like radiation shield 190 that hangs down between the X-ray source 102 and the floor to stop scattered X-ray radiation. This radiation shield 190 may be used separately or in combination with one of the embodiments of the radiation protection device described herein.

Figure 25:
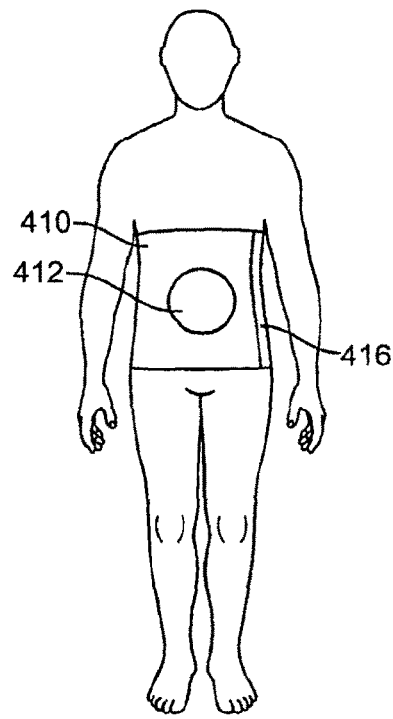
FIG. 25 is an anterior view of a patient wearing a radiation protection garment for use with the radiation protection device of the present invention.
Figure 26:
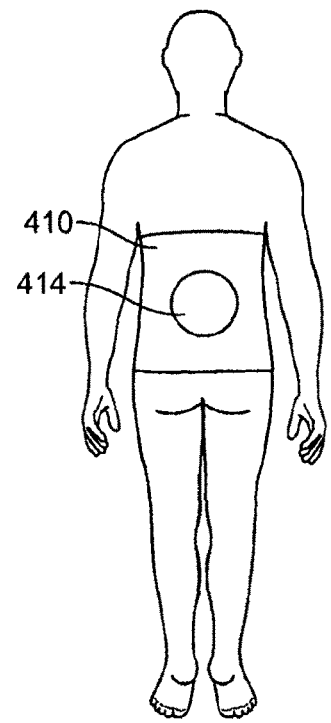
FIG. 26 is a posterior view of the patient wearing a radiation protection garment of FIG. 25.

Alternatively or in addition to the blanket-like radiation shield, the radiation protection device may include a garment-like radiation shield that covers the patient in the area surrounding where the X-ray beam enters the body. FIG. 25 is an anterior view and FIG. 26 is a posterior view of a patient wearing a radiation protection garment 410 in the form of a broad belt made of X-ray opaque material. The belt-shaped radiation protection garment 410 substantially covers the patient's abdomen and a portion of the thorax. There is a fenestration 412 through the anterior portion of the belt-shaped radiation protection garment 410 in the area of the patient's anatomy to be imaged, in this example, the patient's abdomen. Likewise, there is a fenestration 414 through the posterior portion of the belt-shaped radiation protection garment 410, generally opposite to the fenestration 412 in the front. The belt-shaped radiation protection garment 410 is preferably made from a flexible X-ray opaque material. Preferably, a simple-to-operate fastener 416, such as a hook-and-loop fastener, a zipper or a magnetic fastener, is provided on the belt-shaped radiation protection garment 410 for putting the garment on and taking it off of the patient. The fact that the radiation protection garment 410 surrounds the portion of the patient to be exposed to the X-ray beam effectively blocks any stray radiation being emitted from the flanks of the patient. Optionally, the radiation protection garment 410 may fasten to one or both of the radiation shields of the radiation protection device.

Figure 27:
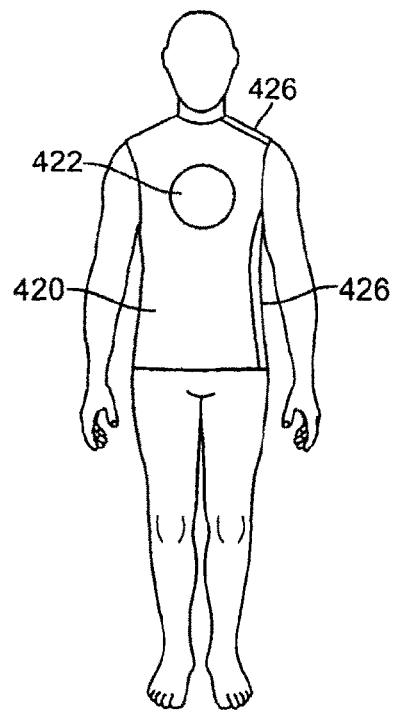
FIG. 27 is an anterior view of a patient wearing a radiation protection garment for use with the radiation protection device of the present invention.
Figure 28:
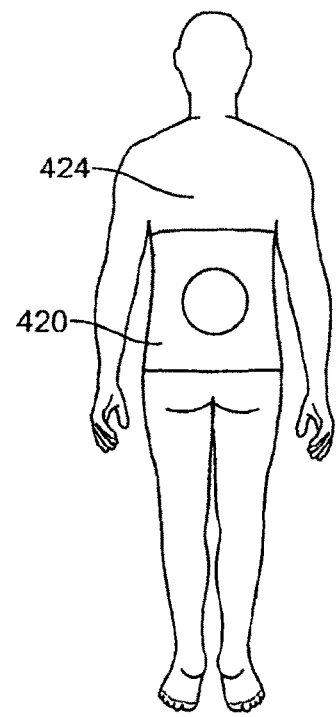
FIG. 28 is a posterior view of the patient wearing a radiation protection garment of FIG. 27.

FIG. 27 is an anterior view and FIG. 28 is a posterior view of a patient wearing a radiation protection garment 420 in the form of a vest made of X-ray opaque material. The vest-shaped radiation protection garment 420 extends from the patient's neck and shoulders to the patient's waist and hips or lower. There is a fenestration 422 through the anterior portion of the vest-shaped radiation protection garment 420 in the area of the patient's anatomy to be imaged, in this example, the patient's thorax. Likewise, there is a fenestration 424 through the posterior portion of the vest-shaped radiation protection garment 420, generally opposite to the fenestration 422 in the front. The vest-shaped radiation protection garment 420 is preferably made from a flexible X-ray opaque material. Preferably, a simple-to-operate fastener 426, such as a hook-and-loop fastener, a zipper or a magnetic fastener, is provided on the vest-shaped radiation protection garment 420 for putting the garment on and taking it off of the patient. The fact that the radiation protection garment 420 surrounds the portion of the patient to be exposed to the X-ray beam effectively blocks any stray radiation being emitted from the flanks of the patient. Optionally, the radiation protection garment 420 may fasten to one or both of the radiation shields of the radiation protection device.

Alternatively or in addition, the radiation protection device may be used for protection from other types of radiation, for example gamma rays, that are used in medical or industrial imaging or other diagnostic or therapeutic medical procedures.

Figure 11:
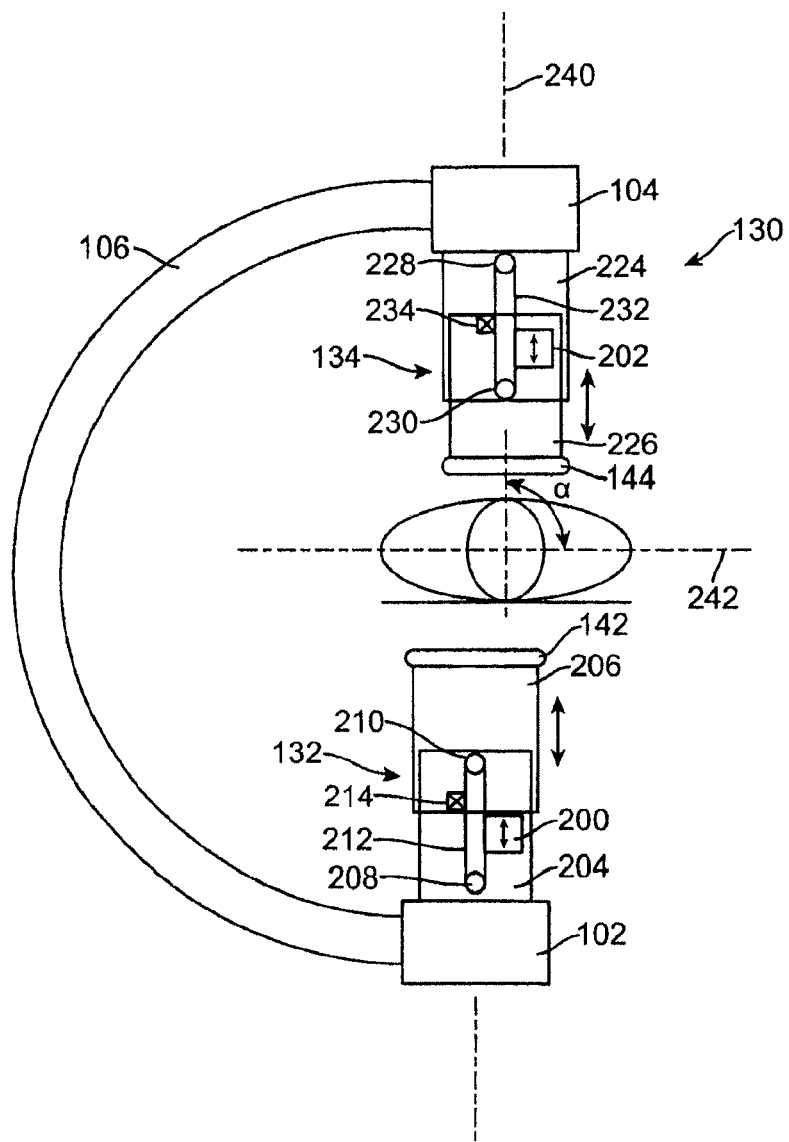
FIG. 11 illustrates a fluoroscope C-arm with a radiation protection device having counterweights connected to the first radiation shield and the second radiation shield.

FIG. 11 illustrates a fluoroscope C-arm 106 with a radiation protection device 130 having a first radiation shield 132 connected to the X-ray source 102 and a second radiation shield 134 connected to the image intensifier 104. The first radiation shield 132 is configured with a first stationary shield 204 adjacent to the X-ray source 102 and a first moving shield 206 that moves telescopically with respect to the first stationary shield 204. The first stationary shield 204 will generally be cylindrical in shape, and the first moving shield 206 will generally be cylindrical or conical in shape. A first flexible and/or inflatable conforming pad 142 is mounted around the opening on the inner end of the first moving shield 206. A first inner pulley 208 is mounted adjacent to the inner edge of the first stationary shield 204 and a first outer pulley 210 is mounted adjacent to the outer edge of the first stationary shield 204. The first inner pulley 208 and the first outer pulley 210 may be mounted directly on the first stationary shield 204 or they may be mounted on a structure that is fixed with respect to the first stationary shield 204. (Note that the designations of "outer" and "inner" are given with respect to the center of the C-arm 106 where the patient is positioned, as shown in the illustration.) A continuous first loop of cable 212, or the like, loops around the first inner pulley 208 and the first outer pulley 210. The first loop of cable 212 is attached adjacent to the inner edge of the first moving shield 206 at a first attachment point 214. The first loop of cable 212 is also attached to a first counterweight 200 at a point approximately 180 degrees apart from the first attachment point 214 on the first loop of cable 212. As the first moving shield 206 moves inward, the first counterweight 200 moves outward, and vise versa. The first counterweight 200 is sized to counteract all or a portion of the weight of the first moving shield 206, which reduces the force required to move the first moving shield 206. Movement of the first moving shield 206 can be active, e.g. with a motor or another actuator mechanism, or it may be passive, e.g. with a light spring that urges the first moving shield 206 inward toward the extended position (upward in the illustration).

Similarly, the second radiation shield 134 is configured with a second stationary shield 224 adjacent to the image intensifier 104 and a second moving shield 226 that moves telescopically with respect to the second stationary shield 224. The second stationary shield 224 will generally be cylindrical in shape, and the second moving shield 226 will generally be cylindrical or conical in shape. A second flexible and/or inflatable conforming pad 144 is mounted around the opening on the inner end of the second moving shield 226. A second inner pulley 228 is mounted adjacent to the inner edge of the second stationary shield 224 and a second outer pulley 230 is mounted adjacent to the inner edge of the second stationary shield 224. The second inner pulley 228 and the second outer pulley 230 may be mounted directly on the second stationary shield 224 or they may be mounted on a structure that is fixed with respect to the second stationary shield 224. A continuous second loop of cable 232, or the like, loops around the second inner pulley 228 and the second outer pulley 230. The second loop of cable 232 is attached adjacent to the inner edge of the second moving shield 226 at a second attachment point 234. The second loop of cable 232 is also attached to a second counterweight 202 at a point approximately 180 degrees apart from the second attachment point 234 on the second loop of cable 232. As the second moving shield 226 moves inward, the second counterweight 202 moves outward, and vise versa. The second counterweight 202 is sized to counteract all or a portion of the weight of the second moving shield 206, which reduces the force required to move the second moving shield 206. Movement of the second moving shield 206 can be active, e.g. with a motor or another actuator mechanism, or it may be passive, e.g. with a light spring that urges the second moving shield 206 inward toward the extended position (downward in the illustration).

The configuration of the counterweight system automatically compensates for changes in the angle of the fluoroscope C-arm 106 because the effective weight of the first and second moving shields 206, 226, as well as the first and second counterweights 200, 202, will be proportional to the sine of the angle .alpha. between the imaging axis 240 of the fluoroscope C-arm 106 and a horizontal axis 242. A counterweighting system depending on springs, or the like, to counteract the weight of the first and second moving shields 206, 226 would not automatically compensate for changes in the angle of the fluoroscope C-arm 106 in the same way. The continuous loop configuration of the first and second cables 212, 232 assures that the cables 212, 232 always operate in tension no matter what angle the fluoroscope C-arm 106 is positioned at, even when the C-arm 106 is inverted. The pulleys and cables of the counterweight system may also be utilized as part of an actuator mechanism for extending and retracting the first and second radiation shields 132 134.

FIG. 11 also illustrates another optional feature of the radiation protection device 130. The first radiation shield 132 is configured such that the first moving shield 206 is larger in diameter than the first stationary shield 204 and moves telescopically on the outside of the first stationary shield 204. Conversely, the second radiation shield 134 is configured such that the second moving shield 226 is smaller in diameter than the second stationary shield 224 and moves telescopically on the inside of the second stationary shield 224. This arrangement assures that X-rays originating from the X-ray source 102 cannot escape the first radiation shield 132 through the gap between the first moving shield 206 and the first stationary shield 204. Similarly, X-rays entering the inner end of the second radiation shield 134 is cannot escape through the gap between the second moving shield 226 and the second stationary shield 224. Alternatively, the radiation protection device 130 may utilize special joints, such as the overlapping flange joints described in connection with FIGS. 15-18, to contain the X-ray beam.

Alternatively, the radiation protection device 130 can be configured so that it is self-counterbalancing, that is, the first radiation shield 132 and the second radiation shield 134 counterbalance each other without the addition of separate counterweights, as in the previous example in FIG. 11. One advantage of this is that it reduces the force needed to extend and retract the first and second radiation shields 132, 134 without the additional weight of separate counterweights. It also provides a simple means to extend and retract the first and second radiation shields 132, 134 in unison.

Figure 12:
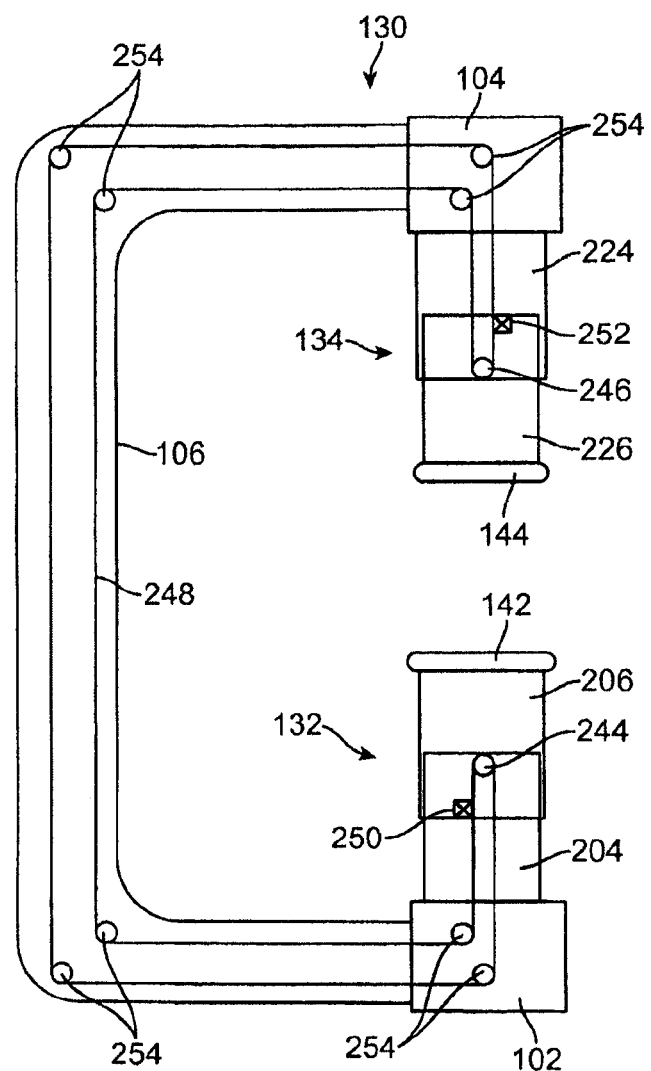
FIG. 12 illustrates a fluoroscope C-arm with a radiation protection device wherein the first radiation shield and the second radiation shield act as counterweights to each other via a cable and pulley connection system.

FIG. 12 illustrates a fluoroscope C-arm 106 with a radiation protection device 130 wherein the first radiation shield 132 and the second radiation shield 134 act as counterweights to each other via a cable and pulley connection system. The first and second radiation shields 132, 134 are configured similarly to the previous example in FIG. 11. A first pulley 244 is mounted adjacent to the inner edge of the first stationary shield 204. The first pulley 244 may be mounted directly on the first stationary shield 204 or it may be mounted on a structure that is fixed with respect to the first stationary shield 204. A second pulley 246 is mounted adjacent to the inner edge of the second stationary shield 224. The second pulley 246 may be mounted directly on the second stationary shield 224 or it may be mounted on a structure that is fixed with respect to the second stationary shield 224. A continuous loop of cable 248 loops around the first pulley 244 and the second pulley 246, passing around the C-arm 106 from the first radiation shield 132 to the second radiation shield 134. A series of additional pulleys 254 support the continuous loop of cable 248 as it passes around the C-arm 106. The number and configuration of additional pulleys 254 needed depends on the geometry of the C-arm 106. Alternatively, push-pull cables with a low-friction coaxial sheath may be used to connect the continuous loop of cable 248 as it passes around the C-arm 106. The continuous loop of cable 248 is attached adjacent to the inner edge of the first moving shield 206 at a first attachment point 250 and is also attached adjacent to the inner edge of the second moving shield 226 at a second attachment point 252, which is on the opposite side of the first pulley 244 and the second pulley 246 from the first attachment point 250. This configuration assures that the first radiation shield 132 and the second radiation shield 134 will extend and retract in unison, with the weight of the first moving shield 206 and the weight of the second moving shield 226 counterbalancing each other. The continuous loop configuration of the cable 248 assures that the cables 212, 232 always operate in tension no matter what angle the fluoroscope C-arm 106 is positioned at, even when the C-arm 106 is inverted. Movement of the first and second moving shields 206, 226 can be active, e.g. with a motor or another actuator mechanism, or it may be passive, e.g. with a light spring that urges the first and second moving shields 206, 226 inward toward the extended position. The pulleys and cables of the self-counterweighting system may also be utilized as part of an actuator mechanism for extending and retracting the first and second radiation shields 132 134. As with the example in FIG. 11, the configuration of the self-counterweighting system automatically compensates for changes in the angle of the fluoroscope C-arm 106 because the effective weight of the first and second moving shields 206, 226 will be proportional to the sine of the angle .alpha. between the imaging axis 240 of the fluoroscope C-arm 106 and a horizontal axis 242.

Figure 13:
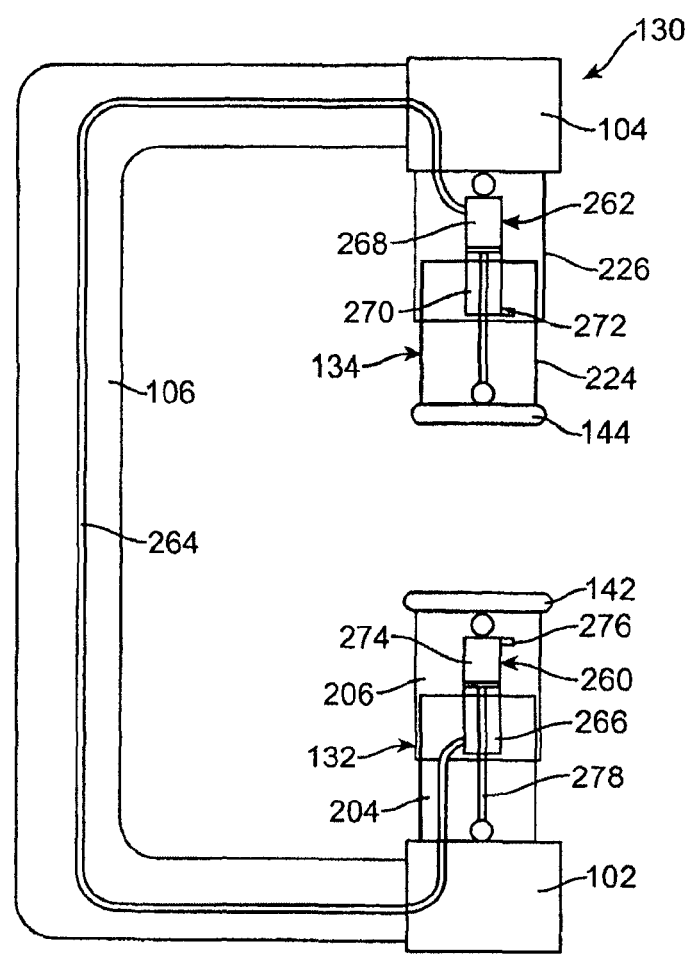
FIG. 13 illustrates a fluoroscope C-arm with a radiation protection device wherein the first radiation shield and the second radiation shield act as counterweights to each other via a pneumatic or hydraulic connection system.

A self-counterbalancing radiation protection device 130 can also be accomplished using a pneumatic or hydraulic connection system. FIG. 13 illustrates a fluoroscope C-arm 106 with a radiation protection device 130 wherein the first radiation shield and the second radiation shield act as counterweights to each other via such a pneumatic or hydraulic connection system. The first and second radiation shields 132, 134 are configured similarly to the example in FIG. 12. A first pneumatic or hydraulic cylinder 260 is connected between the first stationary shield 204 and the first moving shield 206. A second pneumatic or hydraulic cylinder 262 is connected between the second stationary shield 224 and the second moving shield 226. Connection points can be any convenient points on the stationary shields 204, 224 and moving shields 206, 226 that will allow the desired range of motion. For example, pneumatic or hydraulic cylinders 260, 262 may be connected at the outer ends of the stationary shields 204, 224 and the outer ends of the moving shields 206, 226, as shown in FIG. 13. A connection tube 264 makes a fluid connection between the rod end 266 of the first pneumatic or hydraulic cylinder 260 and the cylinder head end 268 of the second pneumatic or hydraulic cylinder 262, or vise versa. The cylinder head end 274 of the first pneumatic or hydraulic cylinder 260 has a first vent 276 and the rod end 270 of the second pneumatic or hydraulic cylinder 262 has a second vent 272. Connecting between opposite ends of the first and second pneumatic or hydraulic cylinders 260, 262 assures that the first and second radiation shields 132, 134 will extend and retract in unison, with the weight of the first moving shield 206 and the weight of the second moving shield 226 counterbalancing each other. Naturally, at least the first pneumatic or hydraulic cylinder 260 must be a double-acting cylinder, or the like, that can be pressurized from the rod end 266 of the cylinder. The first pneumatic or hydraulic cylinder 260 may be slightly larger in diameter than the second pneumatic or hydraulic cylinder 262 to compensate for the area of the rod 278 so that the first moving shield 206 and the second moving shield 226 will move at the same speed and distance. Alternatively, the first and second pneumatic or hydraulic cylinders 260, 262 may be of different diameters chosen to provide a predetermined ratio of the speed and distance moved by the first and second moving shields 206, 226.

Using hydraulic cylinders for the connection system will provide more precise coordination of the movement of the first and second moving shields 206, 226. On the other hand, using pneumatic cylinders for the connection system will provide a spring action that will compensate somewhat for different distances that the first and second moving shields 206, 226 must move depending on the imaging angle and the anatomy of the patient. If pneumatic cylinders are used, it may be desirable to prepressurize the connection system for a stronger spring action and therefore a more immediate response of the counterbalancing function. Movement of the first and second moving shields 206, 226 can be active, e.g. with a motor or another actuator mechanism, or it may be passive, e.g. with a light spring that urges the first and second moving shields 206, 226 inward toward the extended position.

Figure 14:
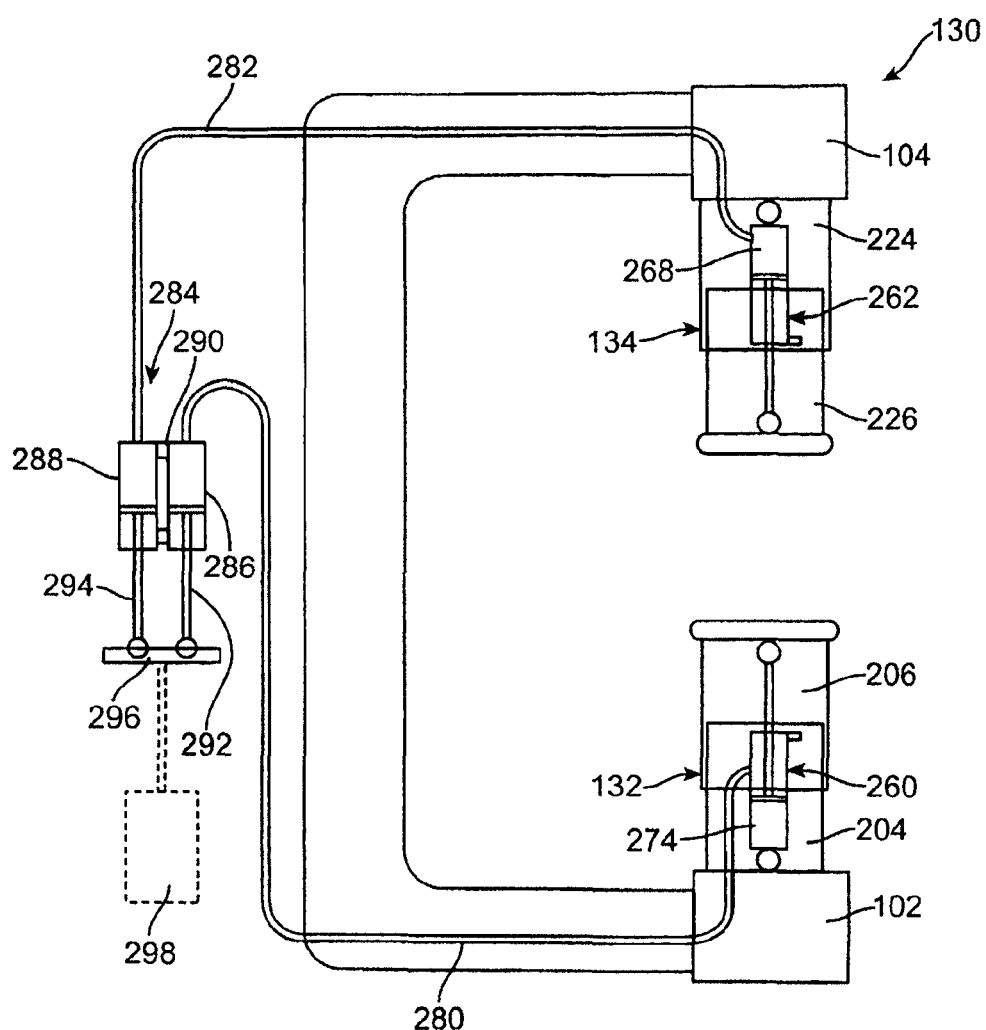
FIG. 14 illustrates a fluoroscope C-arm with a radiation protection device wherein the first radiation shield and the second radiation shield act as counterweights to each other via a pneumatic or hydraulic connection system.

FIG. 14 illustrates a fluoroscope C-arm 106 with a radiation protection device 130 wherein the first radiation shield 132 and the second radiation shield 134 act as counterweights to each other via another configuration of a pneumatic or hydraulic connection system. The first and second radiation shields 132, 134 are configured similarly to the example in FIG. 13. A first pneumatic or hydraulic cylinder 260 is connected between the first stationary shield 204 and the first moving shield 206. A second pneumatic or hydraulic cylinder 262 is connected between the second stationary shield 224 and the second moving shield 226. A first connection tube 280 makes a fluid connection between the cylinder head end 274 of the first pneumatic or hydraulic cylinder 260 and a pressure-to-suction converter 284. A second connection tube 282 makes a fluid connection between the cylinder head end 268 of the second pneumatic or hydraulic cylinder 262 and the pressure-to-suction converter 284. For this application, the first and second pneumatic or hydraulic cylinders 260, 262 can both be configured as single-acting cylinders.

The pressure-to-suction converter 284 in this example is configured with a third pneumatic or hydraulic cylinder 286 and a fourth pneumatic or hydraulic cylinder 288 arranged parallel to one another. There is a mechanical connection 290 between the third pneumatic or hydraulic cylinder 286 and the fourth pneumatic or hydraulic cylinder 288. Similarly, there is a mechanical connection 296 between the rod 292 of the third pneumatic or hydraulic cylinder 286 and the rod 294 of the fourth pneumatic or hydraulic cylinder 288, so that the third and fourth pneumatic or hydraulic cylinders 286, 288 will extend and retract in unison. The first connection tube 280 makes a fluid connection with the cylinder head end of the third pneumatic or hydraulic cylinder 286 and the second connection tube 282 makes a fluid connection with the cylinder head end of the fourth pneumatic or hydraulic cylinder 288. The result of this configuration is that pressure in the cylinder head end 274 of the first pneumatic or hydraulic cylinder 260 due to the weight of the first moving shield 206 will be transmitted through the first connection tube 280 to the pressure-to-suction converter 284; then the pressure-to-suction converter 284 converts the pressure into suction (or negative pressure) and transmits this suction through the second connection tube 282 to the cylinder head end 268 of the second pneumatic or hydraulic cylinder 262, which lifts the second moving shield 226. Thus, the first and second radiation shields 132, 134 will extend and retract in unison, with the weight of the first moving shield 206 and the weight of the second moving shield 226 counterbalancing each other.

Movement of the first and second moving shields 206, 226 can be active, e.g. with a motor or another actuator mechanism, or it may be passive, e.g. with a light spring that urges the first and second moving shields 206, 226 inward toward the extended position. Another option would be to utilize the pneumatic or hydraulic connection system as part of an actuator mechanism for actively extending and retracting the first and second radiation shields 132 134. For example, a motor or linear actuator 298 could be used for moving the rods 292, 294 of the third and fourth pneumatic or hydraulic cylinders 286, 288 to actively extend and retract the first and second radiation shields 132 134 in unison, with the weight of the first moving shield 206 and the weight of the second moving shield 226 counterbalancing each other through the pneumatic or hydraulic connection system.

As in the previous example, using hydraulic cylinders for the connection system will provide more precise coordination of the movement of the first and second moving shields 206, 226, but using pneumatic cylinders for the connection system will provide a spring action that will compensate somewhat for different distances that the first and second moving shields 206, 226 must move depending on the imaging angle and the anatomy of the patient. If pneumatic cylinders are used, it may be desirable to pressurize the connection system for a stronger spring action and therefore a more immediate response of the counterbalancing function.

Although the counterweight systems described above are shown used with telescoping radiation shields, the counterweight systems may also be used with other configurations of radiation shields, such as flexible bellows-shaped radiation shields.

Figure 15:
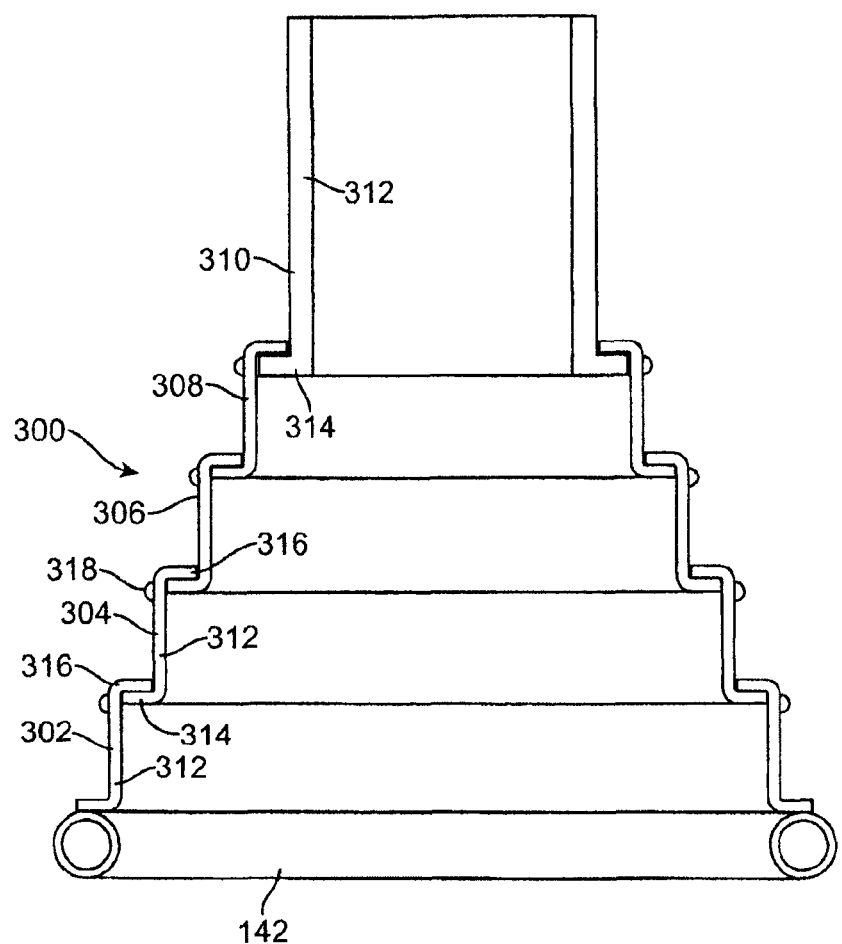
FIG. 15 illustrates an articulated conical radiation shield shown in a fully extended position.
Figure 16:
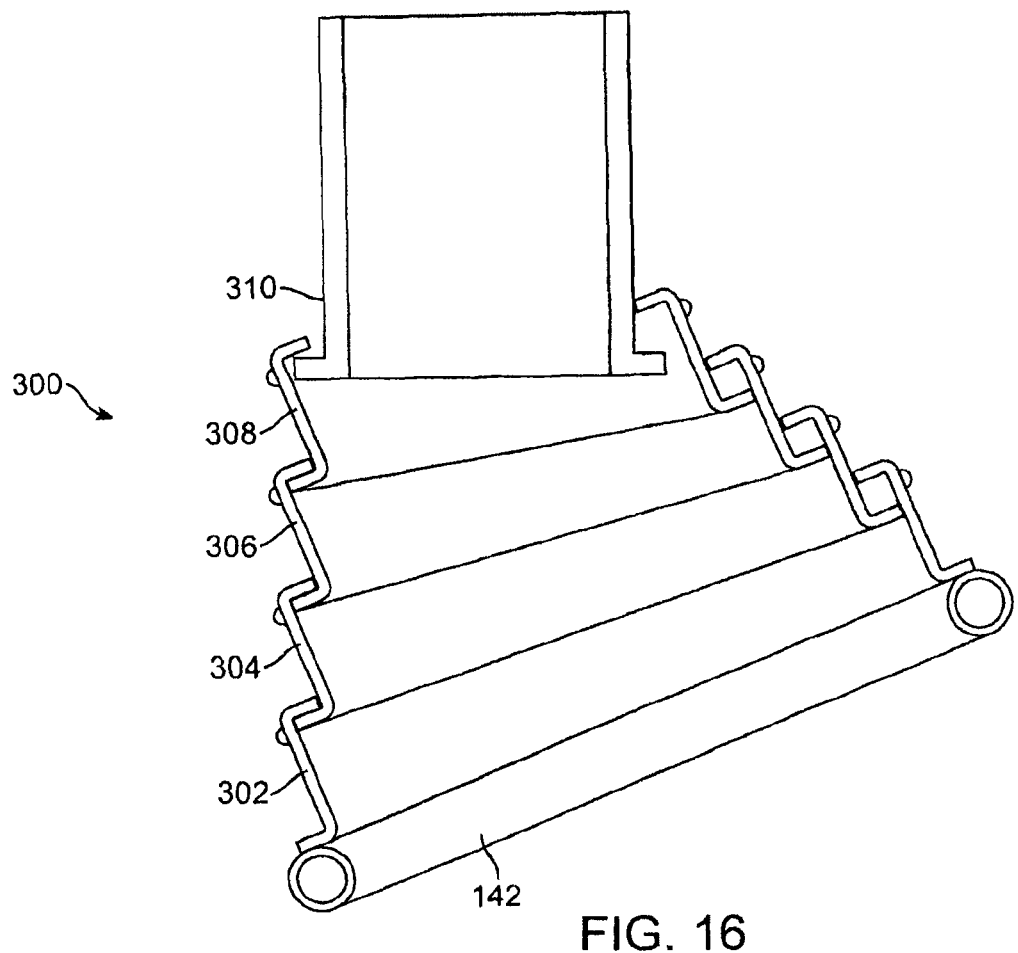
FIG. 16 illustrates the articulated conical radiation shield of FIG. 15 shown in an angled position.

FIGS. 15-16 are cross section views of an articulated conical radiation shield 300 that can be used for the first and/or second radiation shields 132, 134 in various embodiments of the radiation protection device 130 described herein. The articulated conical radiation shield 300 is constructed with multiple telescoping elements 302, 304, 306, 308, 310. The outermost telescoping element 310 is connected to the X-ray source 102 or the image intensifier 104. Each of the intermediate telescoping elements 304, 306, 308 is configured with an approximately cylindrical or conical wall 312 with a flange 314 on the inner end that extends radially outward and a flange 316 on the outer end that extends radially inward. The outermost telescoping element 310 need only include the cylindrical or conical wall 312 and the flange 314 on the inner end that extends radially outward, whereas the innermost telescoping element 302 need only include the cylindrical or conical wall 312 and the flange 316 on the outer end that extends radially inward. A flexible and/or inflatable conforming pad 142 is mounted around the opening on the inner end of the innermost telescoping element 302. (Note that the designations of "outer" and "inner" are given with respect to the center of the C-arm 106 where the patient is positioned.)

The telescoping elements 302, 304, 306, 308, 310, which may vary in number, are stacked together in a telescoping manner, as shown in FIG. 15. Each of the telescoping elements 302, 304, 306, 308, 310 is progressively smaller in diameter moving from the innermost telescoping element 302 to the outermost telescoping element 310, giving an overall conical configuration to the radiation shield 300. The telescoping elements 302, 304, 306, 308, 310 allow the radiation shield 300 to extend and retract and angulate. Optionally, detents 318 may be provided on the outside surface of the telescoping elements 302, 304, 306, 308, 310 near the outer edge of the cylindrical or conical wall 312 to prevent the stack of elements from retracting too far and becoming disconnected.

FIG. 15 shows the articulated conical radiation shield 300 in a fully extended position and FIG. 16 shows the articulated conical radiation shield 300 in an angled position. In all positions of the radiation shield 300, the overlapping flanges 314, 316 create a baffle that prevents X-rays from escaping though the sliding gaps between the telescoping elements 302, 304, 306, 308, 310.

Figure 17:
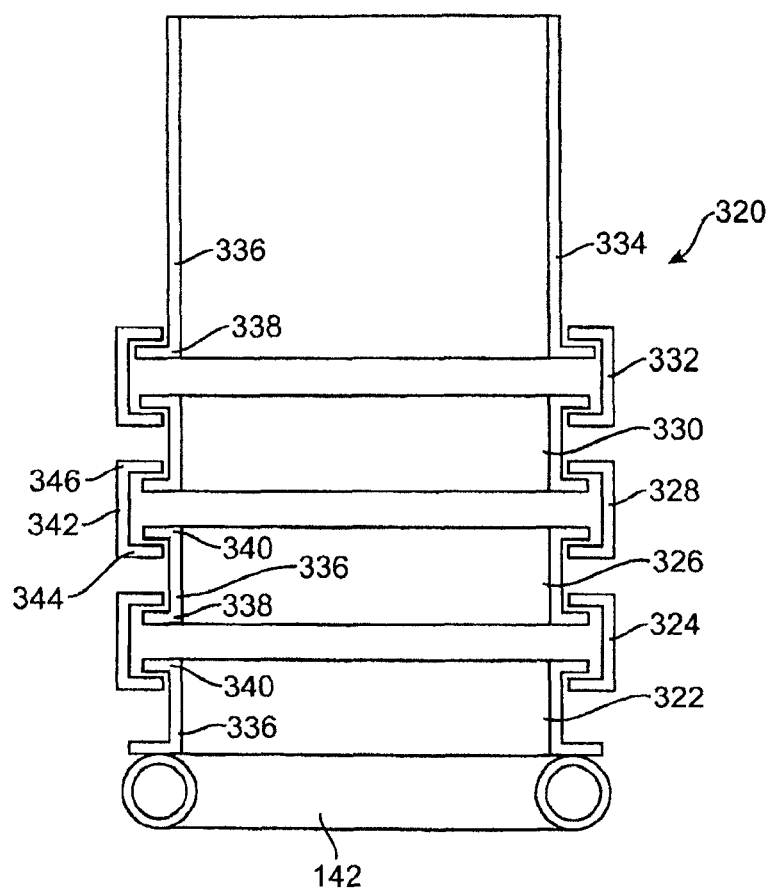
FIG. 17 illustrates an articulated cylindrical radiation shield shown in a fully extended position.
Figure 18:
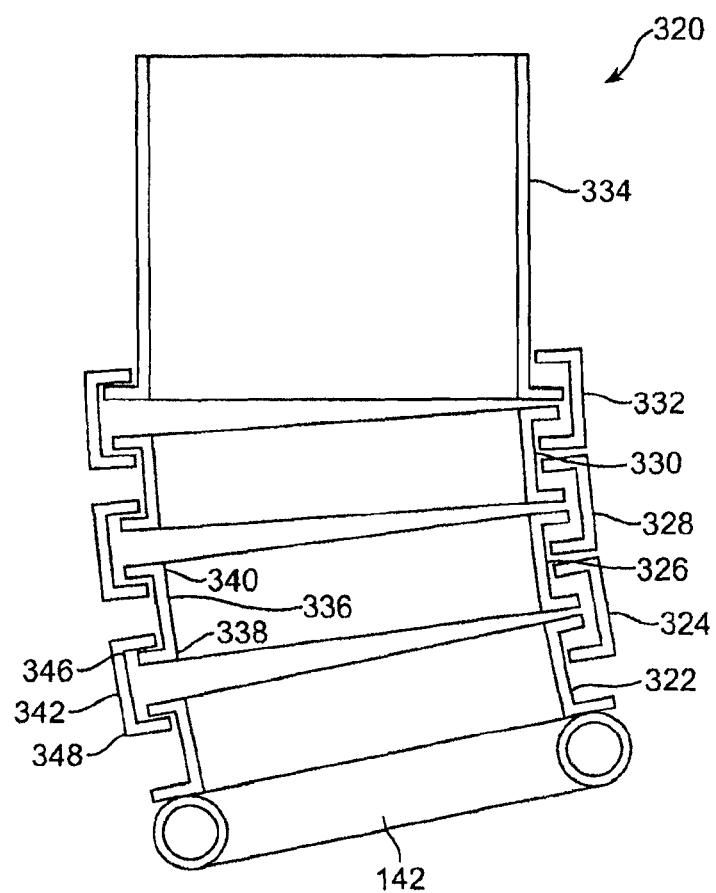
FIG. 18 illustrates the articulated cylindrical radiation shield of FIG. 17 shown in an angled position.

FIGS. 17-18 are cross section views of an articulated cylindrical radiation shield 320 that can be used for the first and/or second radiation shields 132, 134 in various embodiments of the radiation protection device 130 described herein. The articulated cylindrical radiation shield 320 is constructed with multiple telescoping elements 322, 324, 326, 328, 330, 332, 334. The outermost telescoping element 334 is connected to the X-ray source 102 or the image intensifier 104. The multiple telescoping elements are of two general types: inside ring telescoping elements 322, 326, 330, 334 and outside ring telescoping elements 324, 328, 332. Each of the intermediate inside ring telescoping elements 326, 330 is configured with an approximately cylindrical wall 336 with a flange 338 on the inner end that extends radially outward and a flange 340 on the outer end that extends radially outward. The outermost inside ring telescoping element 322 need only include the cylindrical wall 336 and the flange 340 on the inner end that extends radially outward, whereas the innermost inside ring telescoping element 334 need only include the cylindrical wall 336 and the flange 338 on the outer end that extends radially outward. Each of the outside ring telescoping elements 324, 328, 332 is configured with an approximately cylindrical wall 342 with a flange 344 on the inner end that extends radially inward and a flange 346 on the outer end that extends radially inward.

The telescoping elements 322, 324, 326, 328, 330, 332, 334, which may vary in number, are stacked together in an interlocking and telescoping manner, giving an overall cylindrical configuration to the radiation shield 320, as shown in FIG. 17. The outside ring telescoping elements 324, 328, 332 are preferably configured as split rings to facilitate assembly of the radiation shield 320. A flexible and/or inflatable conforming pad 142 is mounted around the opening on the inner end of the innermost telescoping element, which in the example shown is an inside ring telescoping element 334. The telescoping elements 322, 324, 326, 328, 330, 332, 334 allow the radiation shield 320 to extend and retract and angulate.

FIG. 17 shows the articulated cylindrical radiation shield 320 in a fully extended position, and FIG. 18 shows the articulated cylindrical radiation shield 320 in an angled position. In all positions of the radiation shield 320, the overlapping flanges 338, 340, 344, 346 create a baffle that prevents X-rays from escaping though the sliding gaps between the telescoping elements 322, 324, 326, 328, 330, 332, 334.

Figure 19:
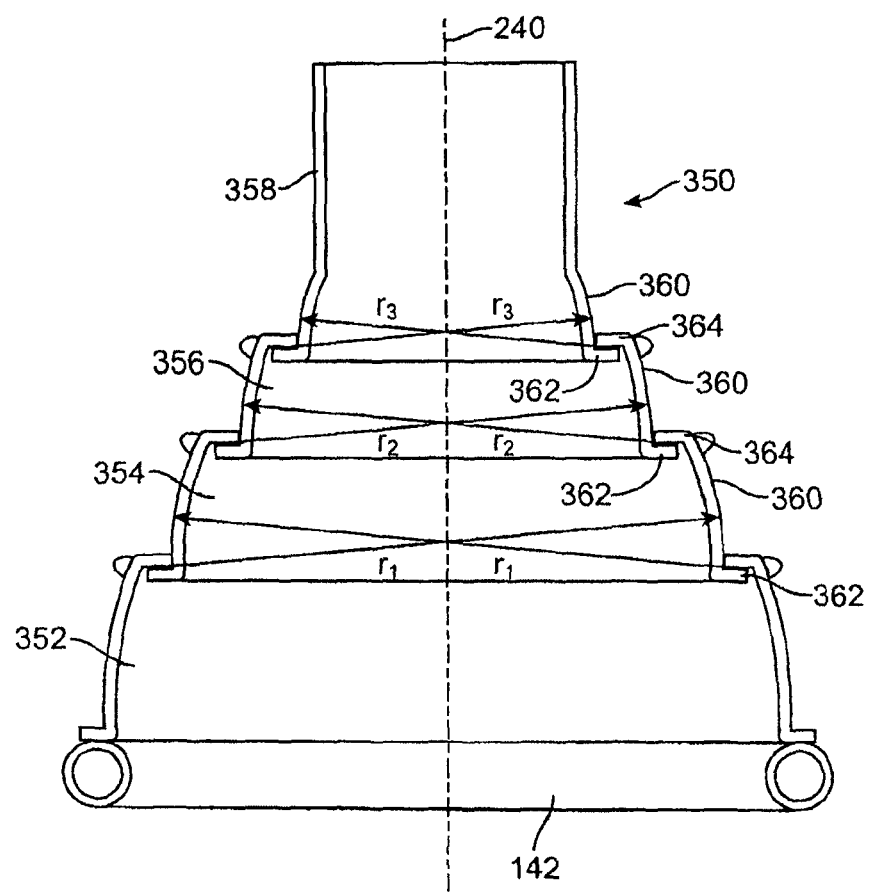
FIG. 19 illustrates an articulated conical radiation shield with telescoping dome-shaped shield elements.

FIG. 19 illustrates an articulated conical radiation shield 350 with telescoping dome-shaped shield elements 352, 354, 356, 358. This embodiment is a variation of the articulated conical radiation shield 300 shown in FIGS. 15-16 and is quite similar in construction. Each of the intermediate telescoping elements 354, 356 is configured with a side wall 360 with a flange 362 on the inner end that extends radially outward and a flange 364 on the outer end that extends radially inward. The side walls 360 have a tapering dome-shaped geometry with a curvature chosen to minimize the gap between adjacent shield elements when the radiation shield 350 is in an angulated position. Looking at shield element 354 as an example, the side wall 360 tapers down in diameter from the inner edge to the outer edge of the side wall 360 with a curvature that can be defined as a surface of rotation made by an arc with a radius r.sub.1 equal to the diameter of the shield element 354 at the junction of the side wall 360 and the flange 362 with the center of the arc located at the junction of the side wall 360 and the flange 362 rotated about the center line 240 of the shield element 354. The side walls 360 of shield elements 356, 358 have similar geometries defined as a surface of rotation made by an arc with a radius r.sub.2, and r.sub.3 respectively rotated about the center line 240 of the shield elements 356, 358. This geometry assures that any gap between the shield elements 352, 354, 356, 358 will remain relatively constant when the radiation shield 350 is in an angulated position. This will enhance the effectiveness of the overlapping flanges 362, 364 to create a baffle that prevents X-rays from escaping though the sliding gaps between the telescoping shield elements 352, 354, 356, 358.

Figure 20:
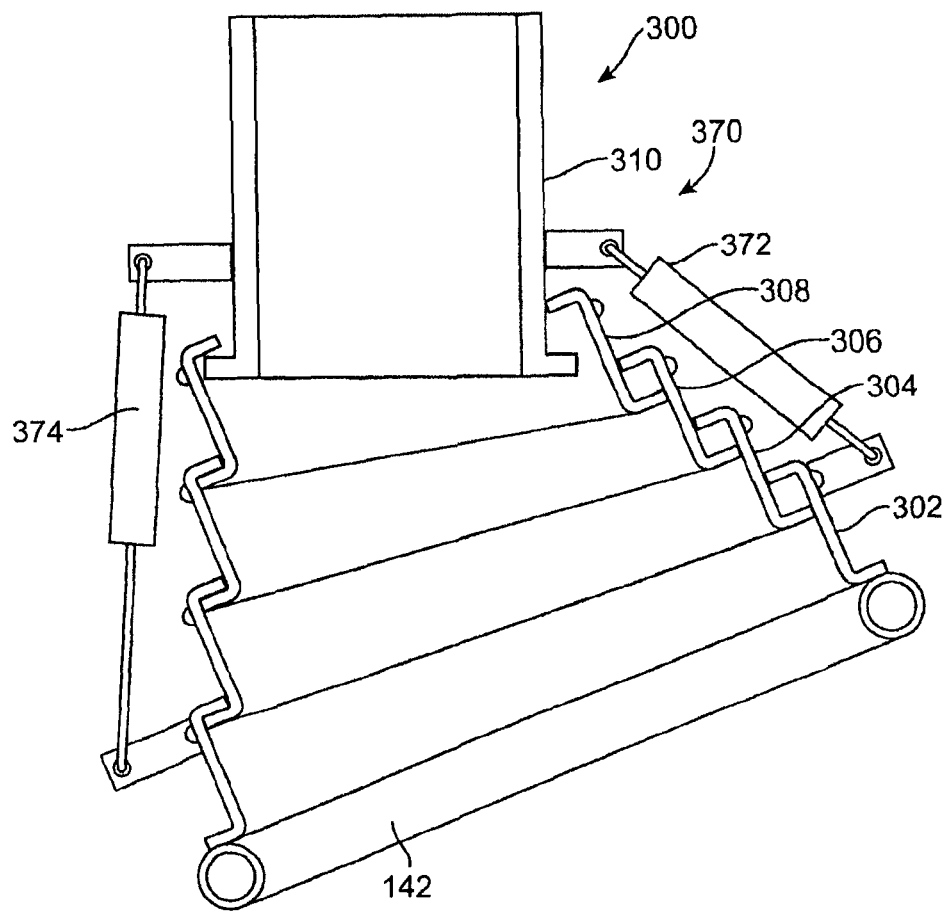
FIG. 20 illustrates an articulated conical radiation shield with an actuation system using linear actuators for extending, retracting and angulating the radiation shield, shown in an angled position.

FIG. 20 illustrates an articulated conical radiation shield 300, similar to the one shown in FIGS. 15-16, with an actuation system 370 using linear actuators 372, 374 for extending, retracting and angulating the radiation shield 300. The actuation system 370 can also be used with various other embodiments of radiation shields described herein. FIG. 20 shows one pair of cooperating linear actuators, including a first linear actuator 372 and a second linear actuator 374 arranged on opposite sides of the radiation shield 300 and connected between the innermost shield element 302 and the outermost shield element 310. Preferably, the actuation system 370 is configured with three or four such linear actuators arranged around the periphery of the radiation shield 300 to provide angulation in all directions. The linear actuators 372, 374 can be hydraulic or pneumatic cylinders, linear motors, motorized lead screws, rack-and-pinion mechanisms, scissors mechanisms, cable-and-pulley mechanisms, solenoids or any other known linear actuator mechanism. The radiation shield 300 is retracted away from the patient by retracting all of the linear actuators 372, 374. Conversely, the radiation shield 300 is extended toward the patient by extending all of the linear actuators 372, 374. To angulate the radiation shield 300, one of the linear actuators 372 is retracted and the other one of the linear actuators 374 is extended, as shown in FIG. 20. The actuation system 370 uses different combinations of extension, retraction and angulation to position the radiation shield 300 between the X-ray source 102 or the image intensifier 104 and the patient for different fluoroscopic views.

Another optional configuration of the actuation system 370 could use multiple smaller linear actuators connected between each pair of adjacent shield elements 302, 304, 306, 308, 310 of the radiation shield 300. The cumulative action of the multiple smaller linear actuators will be equivalent to the three or four large linear actuators in the example described above.

Figure 21:
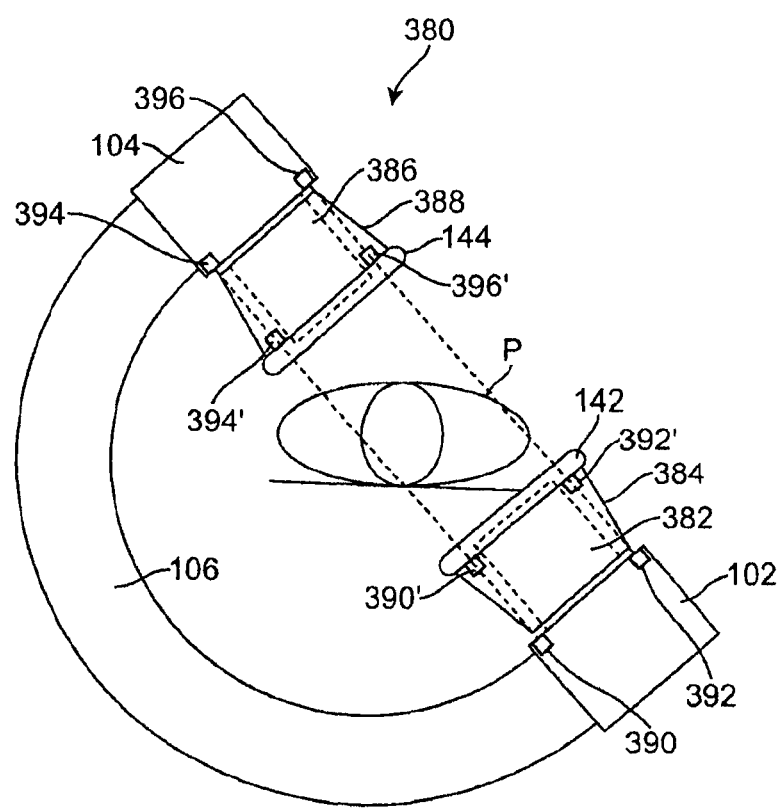
FIG. 21 illustrates a fluoroscope C-arm with a radiation protection device with conical radiation shields shown in a retracted position.

FIG. 21 illustrates a fluoroscope C-arm 106 with a radiation protection device 380 positioned for an oblique fluoroscopic view. The radiation protection device 380 in this example has a cylindrical first stationary shield 382 attached to the X-ray source 102 with a conical first moving shield 384 slidably mounted on it and a cylindrical second stationary shield 386 attached to the image intensifier 104 with a conical second moving shield 388 slidably mounted on it. Optionally, overlapping flanges or other means described herein can be used to prevent X-rays from escaping through any gaps between the moving shields 386, 388 and the stationary shields 382, 384. A first flexible and/or inflatable conforming pad 142 is mounted around the opening on the inner end of the first moving shield 384 and a second flexible and/or inflatable conforming pad 144 is mounted around the opening on the inner end of the second moving shield 388. The first moving shield 384 and the second moving shield 388 are shown in retracted positions. FIG. 21 also illustrates an optional feature that may be used with various embodiments of radiation shields described herein. One or more distance sensors 390, 392, 394, 396 may be used to measure the distance between the X-ray source 102 and/or the image intensifier 104 and the patient P for extending the moving shields 386, 388 the correct distance. If multiple distance sensors 390, 392, 394, 396 are used, the proper angulation for the moving shields 386, 388 can also be determined. The distance sensors 390, 392, 394, 396 may be ultrasonic or laser based distance sensors or other known distance sensors. Alternatively, scanning distance sensors can be used to measure the distance and profile of the patient for determining the correct extension length and angulation for the moving shields 386, 388. The distance sensors 390, 392, 394, 396 may be mounted on the X-ray source 102 and the image intensifier 104 or other fixed position relative to the C-arm 106. Alternatively, distance sensors 390', 392', 394', 396' may be mounted on the moving shields 386, 388. In this case, the distance sensors 390', 392', 394', 396' can be used initially to measure the distance and angle to extend the moving shields 386, 388. Then, as the moving shields 386, 388 approach the patient P, the distance sensors 390', 392', 394', 396' can serve as proximity sensors to determine when to stop extending the moving shields 386, 388 and inflate or extend the first and second conforming pads 142, 144.

Figure 22:
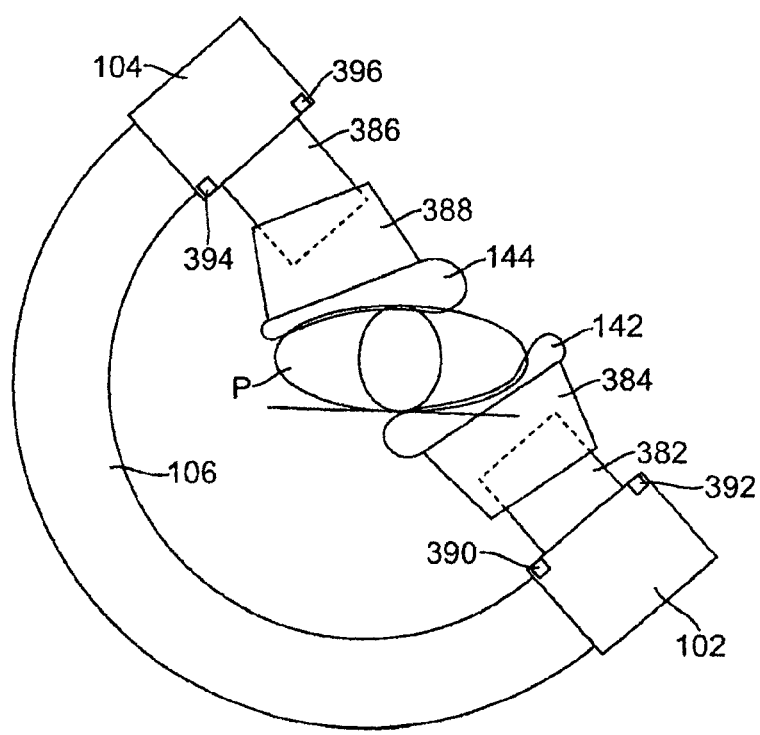
FIG. 22 illustrates a fluoroscope C-arm with the radiation protection device of FIG. 21 with conical radiation shields shown in an extended position.

FIG. 22 illustrates a fluoroscope C-arm 106 with the radiation protection device 380 of FIG. 21 with the conical first and second moving shields 386, 388 shown in an extended position and angulated to approximate the local surface profile of the patient P. The first and second conforming pads 142, 144 have been inflated to close any gaps between the moving shields 386, 388 and the surface of the patient P. Inflation of the conforming pads 142, 144 can be sequenced with the extension of the moving shields 386, 388 or, alternatively, the conforming pads 142, 144 can be always inflated to a low pressure so that they will passively conform to the surface of the patient P.

The radiation protection device 380 may utilize an actuation system 370, such as the one shown in FIG. 20, for movement of the first and second moving shields 386, 388. In addition, the radiation protection device 380 may utilize counterweights or self-counterbalancing to reduce the forces needed to extend and retract the first and second moving shields 386, 388.

Figure 23:
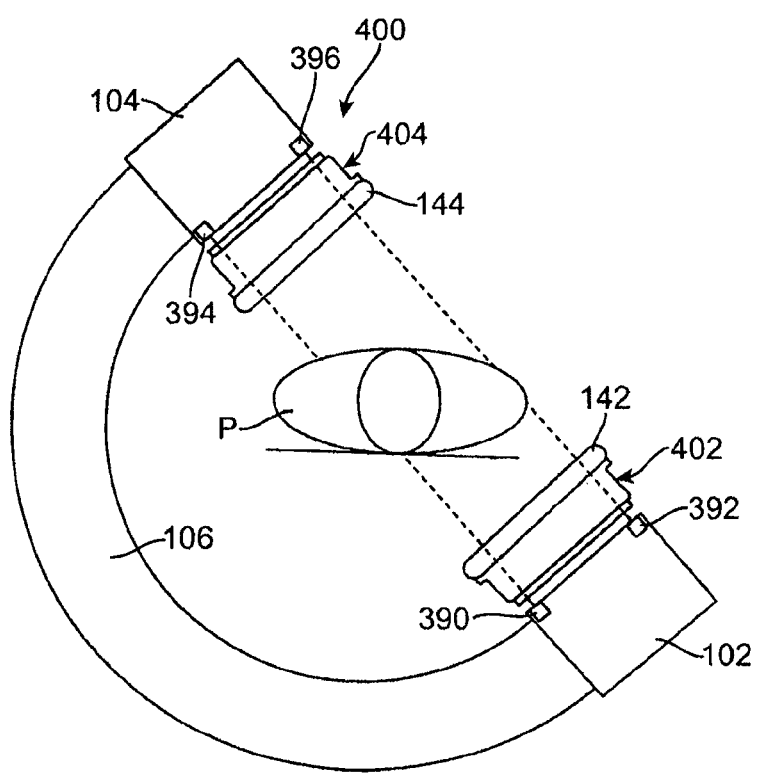
FIG. 23 illustrates a fluoroscope C-arm with a radiation protection device with articulated conical radiation shields shown in a retracted position.

FIG. 23 illustrates a fluoroscope C-arm 106 with a radiation protection device 400 with articulated conical radiation shields 402, 404, similar to the ones shown in FIG. 15-16 or 19. The articulated conical radiation shields 402, 404 are shown in a fully retracted position. Optionally, distance sensors 390, 392, 394, 396 may be used to determine the distance and proper angulation for extending the radiation shields 402, 404.

Figure 24:
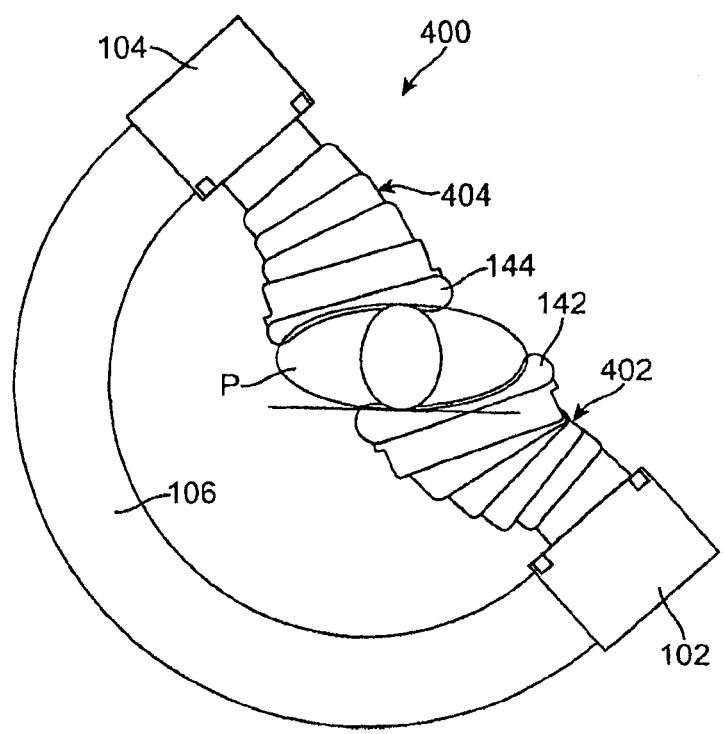
FIG. 24 illustrates a fluoroscope C-arm with the radiation protection device of FIG. 23 with articulated conical radiation shields shown in an extended position.

FIG. 24 illustrates a fluoroscope C-arm 106 with the radiation protection device 400 of FIG. 23 with the articulated conical radiation shields 402, 404 shown in an extended position and angulated to approximate the local surface profile of the patient P. The first and second conforming pads 142, 144 have been inflated to close any gaps between the radiation shields 402, 404 and the surface of the patient P. Inflation of the conforming pads 142, 144 can be sequenced with the extension of the radiation shields 402, 404 or, alternatively, the conforming pads 142, 144 can be always inflated to a low pressure so that they will passively conform to the surface of the patient P.

The radiation protection device 400 may utilize an actuation system 370, such as the one shown in FIG. 20, for movement of the first and second articulated conical radiation shields 402, 404. In addition, the radiation protection device 400 may utilize counterweights or self-counterbalancing to reduce the forces needed to extend and retract the first and second radiation shields 402, 404.

Alternatively or in addition to the distance sensors and proximity sensors described above, the radiation protection device of the resent invention may include a controller that calculates or estimates the proper distance and/or angulation for extending the first and/or second radiation shields based on the position and angle of the desired fluoroscopic view and the anatomic profile of the patient's body. The controller may utilize an electronically implemented algorithm and/or look-up tables to determine the distance and/or angulation for extending the first and/or second radiation shields. This can be implemented by the controller using hardware, software and/or firmware. This feature can be incorporated into an automated version of the radiation protection device, allowing the radiation shields to quickly move to the correct positions for maximal protection of the operator and the patient. The angle and position of the C-arm for the calculation may be measured directly or it may be based on a control command entered by the operator for selection of the C-arm angle and position.

While the radiation protection device has been described for use with C-arm fluoroscopy equipment, the invention can also be used with other imaging and treatment modalities requiring radiation protection. For example, some biplane fluoroscopy imaging systems are configured with an entire circle that supports two X-ray sources and two image intensifiers, rather than a C-arm per se. Other fluoroscopy imaging systems are configured with the X-ray source floor-mounted below the examination table and the image intensifier ceiling-mounted or cantilevered over the patient. The radiation protection device of the present invention can be equally well adapted to these imaging systems, as well as many imaging and treatment systems with other geometries.

Any one of the embodiments of the radiation protection device described herein may also be configured to include a grid, known as a Bucky grid or Bucky-Potter grid, between the patient and the image intensifier to reduce the blurring effect of scattered radiation on the imaging device. An extra long grid may be beneficial to eliminate any scattered radiation that might be caused by the radiation protection device itself.

Since the radiation protection devices of the present invention will add extra weight to the C-arm of the fluoroscope, it may be necessary to reinforce the supporting structures of the C-arm and/or to add ballast or a wider base to the supporting structures to prevent the extra weight from destabilizing the C-arm.

While the present invention has been described herein with respect to the exemplary embodiments and the best mode for practicing the invention, it will be apparent to one of ordinary skill in the art that many modifications, improvements and subcombinations of the various embodiments, adaptations and variations can be made to the invention without departing from the spirit and scope thereof.

What is claimed is:

1. A method for performing fluoroscopy with radiation protection, said method comprising:
   providing an X-ray source and an X-ray detector/image intensifier mounted on a C-arm adjacent a procedure table;
   positioning a first end of a first radiation shield around the X-ray source and extending a second end of the first radiation shield to contact the procedure table or a body of a patient on the procedure table;
   positioning a first end of a second radiation shield around the X-ray detector/image intensifier and extending a second end of the second radiation shield to contact the procedure table or the body of the patient on the procedure table; and
   directing x-rays from the x-ray source through the body of the patient to the X-ray detector/image intensifier while the patient lies on the procedure table within the C-arm, wherein the first radiation shield and the second radiation shield block stray radiation being emitted beyond the body of the patient.

2. The method of claim 1, further comprising retracting the second end of the first radiation shield and the second end of the second radiation shield away from contact with the procedure table or the body of the patient after completion of a fluoroscopic procedure.

3. The method of claim 1, wherein extending a second end of the first radiation shield to contact the procedure table or the body of the patient comprises contacting a first soft, conformable edge surrounding the second end of the first radiation shield against the body of the patient or the table.

4. The method of claim 3, wherein extending a second end of the second radiation shield to contact the procedure table or the body of the patient comprises contacting a second soft, conformable edge surrounding the second end of the second radiation shield against the body of the patient or the table.

5. The method of claim 1, further comprising adjusting a length of the first radiation shield and a length of the second radiation shield to accommodate motion of the C-arm relative to the patient.

6. The method of claim 5, wherein the first radiation shield and the second radiation shield are spring biased to maintain their second ends in contact with the procedure table or the body of the patient on the procedure table to accommodate motion of the C-arm relative to the patient.

7. The method of claim 5, further comprising sensing proximity or initial contact of the second end of the first radiation shield with the procedure table or the body of the patient to control adjusting the length of the first radiation shield.

8. The method of claim 7, further comprising sensing proximity or initial contact of the second end of the second radiation shield with the procedure table or the body of the patient to control adjusting the length of the second radiation shield.

* * * * *